(12) United States Patent
Dong

(10) Patent No.: US 7,811,989 B2
(45) Date of Patent: Oct. 12, 2010

(54) PEPTIDE YY ANALOGS

(75) Inventor: Zheng Xin Dong, Holliston, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 1082 days.

(21) Appl. No.: 10/542,227

(22) PCT Filed: Jan. 13, 2004

(86) PCT No.: PCT/US2004/000892

§ 371 (c)(1),
(2), (4) Date: Apr. 5, 2006

(87) PCT Pub. No.: WO2004/066966

PCT Pub. Date: Aug. 12, 2004

(65) Prior Publication Data

US 2006/0211610 A1    Sep. 21, 2006

Related U.S. Application Data

(60) Provisional application No. 60/440,812, filed on Jan. 17, 2003.

(51) Int. Cl.
*A61K 38/16* (2006.01)
(52) U.S. Cl. .................................... 514/12; 530/324
(58) Field of Classification Search .................. None
See application file for complete search history.

(56) References Cited

U.S. PATENT DOCUMENTS

| | | | |
|---|---|---|---|
| 5,516,653 A | 5/1996 | Bard et al. |
| 5,545,549 A | 8/1996 | Gerald et al. |
| 5,574,010 A | 11/1996 | McFadden |
| 5,602,024 A | 2/1997 | Gerald et al. |
| 5,604,203 A | 2/1997 | Balasubramaniam |
| 5,710,246 A | 1/1998 | Funk et al. |
| 5,912,227 A | 6/1999 | Croom, Jr. et al. |
| 5,916,869 A | 6/1999 | Croom, Jr. et al. |
| 5,968,819 A | 10/1999 | Gerald et al. |
| 5,976,814 A | 11/1999 | Bard et al. |
| 5,989,834 A | 11/1999 | Gerald et al. |
| 5,989,920 A | 11/1999 | Gerald et al. |
| 6,046,167 A | 4/2000 | Balasubramaniam |
| 6,087,154 A | 7/2000 | Baez et al. |
| 6,242,251 B1 | 6/2001 | Baez et al. |
| 6,316,203 B1 | 11/2001 | Gerald et al. |
| 6,355,478 B1 | 3/2002 | Baez et al. |
| 7,157,426 B2 * | 1/2007 | Quay et al. ................ 514/12 |
| 2002/0103123 A1 | 8/2002 | Gerald et al. |
| 2002/0141985 A1 | 10/2002 | Pittner et al. |

FOREIGN PATENT DOCUMENTS

| | | |
|---|---|---|
| EP | 0746332 B1 | 2/2000 |
| EP | 0732875 B1 | 7/2003 |
| WO | WO 93/24515 A1 | 12/1993 |
| WO | 94/19370 | 9/1994 |
| WO | WO 94/22467 A1 | 10/1994 |
| WO | WO 95/17906 A1 | 7/1995 |
| WO | WO 95/21245 A1 | 8/1995 |
| WO | WO 96/14854 A1 | 5/1996 |
| WO | WO 96/16542 A1 | 6/1996 |
| WO | WO 96/22783 A1 | 8/1996 |
| WO | WO 97/46250 A1 | 12/1997 |
| WO | WO 97/48406 A1 | 12/1997 |
| WO | WO 98/20885 A1 | 5/1998 |
| WO | 00/34332 | 6/2000 |
| WO | 01/58409 | 8/2001 |
| WO | WO 01/54486 A1 | 8/2001 |
| WO | WO 02/47712 A2 | 6/2002 |

OTHER PUBLICATIONS

Batterham et al., Nature, 2002, vol. 418- pp. 650-654.*
Balasubramaniam et al., Peptide Research, 1(1):32-35 (1988).
Batterham et al., Nature, 418:650-654 (2002).
Schwartz et al., Nature, 418:595-597 (2002).
Tscöp et al., Nature, 430:165 (2004).
Keire, D. A. et al., "Structure and receptor binding of PYY analogs," Peptides, 2002, 23(2):305-21.

* cited by examiner

*Primary Examiner*—Christopher R. Tate
*Assistant Examiner*—Roy Teller
(74) *Attorney, Agent, or Firm*—Yankwich & Associates; Alan F. Feeney; Tony K. Uhm

(57) ABSTRACT

The invention provides analogs of PYY. The invention also provides compositions and methods useful for controlling biological activities such as cell proliferation, nutrient transport, lipolysis, and intestinal water and electrolyte secretion.

7 Claims, No Drawings

SEQUENCE LISTING

<160> NUMBER OF SEQ ID NOS: 108

<210> SEQ ID NO 1
<211> LENGTH: 36

```
<212> TYPE: PRT
<213> ORGANISM: Artificial Sequence
<220> FEATURE:
<223> OTHER INFORMATION: Human PYY

<400> SEQUENCE: 1

Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 36
<212> TYPE: PRT
<213> ORGANISM: Artificial Sequence
<220> FEATURE:
<223> OTHER INFORMATION: Rat PYY

<400> SEQUENCE: 2

Tyr Pro Ala Lys Pro Glu Ala Pro Gly Glu Asp Ala Ser Pro Glu Glu
 1               5                  10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (29)..(29)
<223> OTHER INFORMATION: Xaa is 1-amino-1-cyclopentanecarboxylic acid
<220> FEATURE:
<221> NAME/KEY: MOD_RES
<222> LOCATION: (34)..(34)
<223> OTHER INFORMATION: C-Terminal Amidation

<400> SEQUENCE: 3

Ile Lys Pro Glu Ala Pro Gly Glu Asp Ala Ser Pro Glu Glu Leu Asn
 1               5                  10                  15

Arg Tyr Tyr Ala Ser Leu Arg His Tyr Leu Asn Leu Xaa Thr Arg Gln
            20                  25                  30

Arg Tyr

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 1-amino-1-cyclopentanecarboxylic acid
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MOD_RES
<222> LOCATION: (15)..(15)
```

<223> OTHER INFORMATION: C-Terminal AMIDATION

<400> SEQUENCE: 4

Xaa Ser Leu Arg His Tyr Leu Asn Leu Val Thr Arg Gln Arg Tyr
1               5                   10                  15

<210> SEQ ID NO 5
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: Xaa is beta-(3-pyridinyl)alanine
<220> FEATURE:
<221> NAME/KEY: MOD_RES
<222> LOCATION: (34)..(34)
<223> OTHER INFORMATION: C-Terminal AMIDATION

<400> SEQUENCE: 5

Ile Lys Pro Glu Ala Pro Gly Glu Asp Ala Ser Pro Glu Glu Leu Asn
1               5                   10                  15

Arg Tyr Tyr Ala Ser Leu Arg Xaa Tyr Leu Asn Leu Val Thr Arg Gln
            20                  25                  30

Arg Tyr

<210> SEQ ID NO 6
<211> LENGTH: 34
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: Xaa is beta-(4-thiazolyl)alanine
<220> FEATURE:
<221> NAME/KEY: MOD_RES
<222> LOCATION: (34)..(34)
<223> OTHER INFORMATION: C-Terminal AMIDATION

<400> SEQUENCE: 6

Ile Lys Pro Glu Ala Pro Gly Glu Asp Ala Ser Pro Glu Glu Leu Asn
1               5                   10                  15

Arg Tyr Tyr Ala Ser Leu Arg Xaa Tyr Leu Asn Leu Val Thr Arg Gln
            20                  25                  30

Arg Tyr

<210> SEQ ID NO 7
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (33)..(33)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 7

Ile Lys Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Leu Val Thr Arg Gln
            20                  25                  30

Xaa Tyr

<210> SEQ ID NO 8
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (26)..(26)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 8

Ile Lys Pro Glu Ala Pro Gly Glu Asp Ala Ser Pro Glu Glu Leu Asn
1               5                   10                  15

Arg Tyr Tyr Ala Ser Leu Arg His Tyr Xaa Asn Leu Val Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (28)..(28)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 9

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Xaa Val Thr Arg Gln
            20                  25                  30

Arg Tyr

<210> SEQ ID NO 10
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (22)..(22)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 10

Ile Lys Pro Glu Ala Pro Gly Glu Asp Ala Ser Pro Glu Glu Leu Asn
1               5                   10                  15
```

```
Arg Tyr Tyr Ala Ser Xaa Arg His Tyr Leu Asn Leu Val Thr Arg Gln
            20                  25                  30

Arg Tyr

<210> SEQ ID NO 11
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (20)..(20)
<223> OTHER INFORMATION: Xaa is alpha-aminoisobutyric acid
<220> FEATURE:
<221> NAME/KEY: MOD_RES
<222> LOCATION: (34)..(34)
<223> OTHER INFORMATION: C-Terminal AMIDATION

<400> SEQUENCE: 11

Ile Lys Pro Glu Ala Pro Gly Glu Asp Ala Ser Pro Glu Glu Leu Asn
1               5                   10                  15

Arg Tyr Tyr Xaa Ser Leu Arg His Tyr Leu Asn Leu Val Thr Arg Gln
            20                  25                  30

Arg Tyr

<210> SEQ ID NO 12
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (25)..(25)
<223> OTHER INFORMATION: Xaa is 3,4,5-trifluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 12

Ile Lys Pro Glu Ala Pro Gly Glu Asp Ala Ser Pro Glu Glu Leu Asn
1               5                   10                  15

Arg Tyr Tyr Ala Ser Leu Arg His Xaa Leu Asn Leu Val Thr Arg Gln
            20                  25                  30

Arg Tyr

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is beta-(4-pyridinyl)alanine
<220> FEATURE:
<221> NAME/KEY: MOD_RES
<222> LOCATION: (15)..(15)
<223> OTHER INFORMATION: C-Terminal AMIDATION

<400> SEQUENCE: 13
```

Ala Ser Leu Arg Xaa Tyr Leu Asn Leu Val Thr Arg Gln Arg Tyr
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is beta-(3-pyridinyl)alanine
<220> FEATURE:
<221> NAME/KEY: MOD_RES
<222> LOCATION: (15)..(15)
<223> OTHER INFORMATION: C-Terminal AMIDATION

<400> SEQUENCE: 14

Ala Ser Leu Arg Xaa Tyr Leu Asn Leu Val Thr Arg Gln Arg Tyr
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (6)..(6)
<223> OTHER INFORMATION: Xaa is 3,4,5-trifluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 15

Ala Ser Leu Arg His Xaa Leu Asn Leu Val Thr Arg Gln Arg Tyr
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is beta-(3-pyridinyl)alanine
<220> FEATURE:
<221> NAME/KEY: MOD_RES
<222> LOCATION: (13)..(13)
<223> OTHER INFORMATION: C-Terminal AMIDATION

<400> SEQUENCE: 16

Leu Arg Xaa Tyr Leu Asn Leu Leu Thr Arg Gln Arg Tyr
1               5                   10

```
<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is beta-(4-pyridinyl)alanine
<220> FEATURE:
<221> NAME/KEY: MOD_RES
<222> LOCATION: (13)..(13)
<223> OTHER INFORMATION: C-Terminal AMIDATION

<400> SEQUENCE: 17

Leu Arg Xaa Tyr Leu Asn Leu Leu Thr Arg Gln Arg Tyr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is beta-(2-pyridinyl)alanine
<220> FEATURE:
<221> NAME/KEY: MOD_RES
<222> LOCATION: (13)..(13)
<223> OTHER INFORMATION: C-Terminal AMIDATION

<400> SEQUENCE: 18

Leu Arg Xaa Tyr Leu Asn Leu Leu Thr Arg Gln Arg Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is beta-(4-thiazolyl)alanine
<220> FEATURE:
<221> NAME/KEY: MOD_RES
<222> LOCATION: (13)..(13)
<223> OTHER INFORMATION: C-Terminal AMIDATION

<400> SEQUENCE: 19

Leu Arg Xaa Tyr Leu Asn Leu Leu Thr Arg Gln Arg Tyr
1               5                   10

<210> SEQ ID NO 20
<211> LENGTH: 15
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is beta-(4-thiazolyl)alanine
<220> FEATURE:
<221> NAME/KEY: MOD_RES
<222> LOCATION: (15)..(15)
<223> OTHER INFORMATION: C-Terminal AMIDATION

<400> SEQUENCE: 20

Ala Ser Leu Arg Xaa Tyr Leu Asn Leu Val Thr Arg Gln Arg Tyr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (10)..(10)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 21

Ala Ser Leu Arg His Tyr Leu Asn Leu Xaa Thr Arg Gln Arg Tyr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (9)..(9)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 22

Ala Ser Leu Arg His Tyr Leu Asn Xaa Val Thr Arg Gln Arg Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
```

```
<222> LOCATION: (1)..(1)
<223> OTHER INFORMATION: N-Terminal ACETYLATION
<220> FEATURE:
<221> NAME/KEY: MISC_FEATURE
<222> LOCATION: (7)..(7)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 23

Ala Ser Leu Arg His Tyr Xaa Asn Leu Val Thr Arg Gln Arg Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (10)..(10)
<223> OTHER INFORMATION: Xaa is 1-amino-1-cyclopentanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 24

Ala Ser Leu Arg His Tyr Leu Asn Leu Xaa Thr Arg Gln Arg Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 25

Ala Ser Xaa Arg His Tyr Leu Asn Leu Val Thr Arg Gln Arg Tyr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
```

```
<222> LOCATION: (5)..(5)
<223> OTHER INFORMATION: Xaa is D-beta-(2-pyridinyl)alanine
<220> FEATURE:
<221> NAME/KEY: MOD_RES
<222> LOCATION: (15)..(15)
<223> OTHER INFORMATION: C-Terminal AMIDATION

<400> SEQUENCE: 26

Ala Ser Leu Arg Xaa Tyr Leu Asn Leu Val Thr Arg Gln Arg Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is beta-(2-pyridinyl)alanine
<220> FEATURE:
<221> NAME/KEY: MOD_RES
<222> LOCATION: (15)..(15)
<223> OTHER INFORMATION: C-Terminal AMIDATION

<400> SEQUENCE: 27

Ala Ser Leu Arg Xaa Tyr Leu Asn Leu Val Thr Arg Gln Arg Tyr
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 1-amino-1-cyclohexanecarboxylic acid
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MOD_RES
<222> LOCATION: (13)..(13)
<223> OTHER INFORMATION: C-Terminal AMIDATION

<400> SEQUENCE: 28

Xaa Arg His Tyr Leu Asn Leu Leu Thr Arg Gln Arg Tyr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is 1-amino-1-cyclohexanecarboxylic acid
<220> FEATURE:
<221> NAME/KEY: MOD_RES
```

```
<222> LOCATION: (13)..(13)
<223> OTHER INFORMATION: C-Terminal AMIDATION

<400> SEQUENCE: 29

Leu Arg His Tyr Xaa Asn Leu Leu Thr Arg Gln Arg Tyr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (8)..(8)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 30

Leu Arg His Tyr Leu Asn Leu Xaa Thr Arg Gln Arg Tyr
1               5                   10

<210> SEQ ID NO 31
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(18)
<223> OTHER INFORMATION: Xaa is 2,3,4,5,6-pentafluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 31

Ile Lys Pro Glu Ala Pro Gly Glu Asp Ala Ser Pro Glu Glu Leu Asn
1               5                   10                  15

Arg Xaa Tyr Ala Ser Leu Arg His Tyr Leu Asn Leu Val Thr Arg Gln
            20                  25                  30

Arg Tyr

<210> SEQ ID NO 32
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (19)..(19)
<223> OTHER INFORMATION: Xaa is 2,3,4,5,6-pentafluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 32

Ile Lys Pro Glu Ala Pro Gly Glu Asp Ala Ser Pro Glu Glu Leu Asn
1               5                   10                  15
```

-continued

Arg Tyr Xaa Ala Ser Leu Arg His Tyr Leu Asn Leu Val Thr Arg Gln
            20                  25                  30

Arg Tyr

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is 2,3,4,5,6-pentafluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 33

Ala Ser Leu Arg Xaa Tyr Leu Asn Leu Val Thr Arg Gln Arg Tyr
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is 2,3,4,5,6-pentafluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 34

Leu Arg Xaa Tyr Leu Asn Leu Val Thr Arg Gln Arg Tyr
1               5                   10

<210> SEQ ID NO 35
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: Xaa is 2,3,4,5,6-pentafluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 35

Ile Lys Pro Glu Ala Pro Gly Glu Asp Ala Ser Pro Glu Glu Leu Asn
1               5                   10                  15

Arg Tyr Tyr Ala Ser Leu Arg Xaa Tyr Leu Asn Leu Val Thr Arg Gln
            20                  25                  30

Arg Tyr

<210> SEQ ID NO 36
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (6)..(6)
<223> OTHER INFORMATION: Xaa is 2,3,4,5,6-pentafluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 36

Ala Ser Leu Arg His Xaa Leu Asn Leu Val Thr Arg Gln Arg Tyr
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (4)..(4)
<223> OTHER INFORMATION: Xaa is 2,3,4,5,6-pentafluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 37

Leu Arg His Xaa Leu Asn Leu Val Thr Arg Gln Arg Tyr
1               5                   10

<210> SEQ ID NO 38
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (25)..(25)
<223> OTHER INFORMATION: Xaa is 2,3,4,5,6-pentafluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 38

Ile Lys Pro Glu Ala Pro Gly Glu Asp Ala Ser Pro Glu Glu Leu Asn
1               5                   10                  15

Arg Tyr Tyr Ala Ser Leu Arg His Xaa Leu Asn Leu Val Thr Arg Gln
            20                  25                  30

Arg Tyr

```
<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (15)..(15)
<223> OTHER INFORMATION: Xaa is 2,3,4,5,6-pentafluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 39

Ala Ser Leu Arg His Tyr Leu Asn Leu Val Thr Arg Gln Arg Xaa
1               5                   10                  15

<210> SEQ ID NO 40
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (13)..(13)
<223> OTHER INFORMATION: Xaa is 2,3,4,5,6-pentafluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 40

Leu Arg His Tyr Leu Asn Leu Val Thr Arg Gln Arg Xaa
1               5                   10

<210> SEQ ID NO 41
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa is 2,3,4,5,6-pentafluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 41

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Xaa

<210> SEQ ID NO 42
<211> LENGTH: 34
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(18)
<223> OTHER INFORMATION: Xaa is 3,4,5-trifluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 42

Ile Lys Pro Glu Ala Pro Gly Glu Asp Ala Ser Pro Glu Glu Leu Asn
1               5                   10                  15

Arg Xaa Tyr Ala Ser Leu Arg His Tyr Leu Asn Leu Val Thr Arg Gln
            20                  25                  30

Arg Tyr

<210> SEQ ID NO 43
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (19)..(19)
<223> OTHER INFORMATION: Xaa is 3,4,5-trifluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 43

Ile Lys Pro Glu Ala Pro Gly Glu Asp Ala Ser Pro Glu Glu Leu Asn
1               5                   10                  15

Arg Tyr Xaa Ala Ser Leu Arg His Tyr Leu Asn Leu Val Thr Arg Gln
            20                  25                  30

Arg Tyr

<210> SEQ ID NO 44
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is 3,4,5-trifluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 44

Ala Ser Leu Arg Xaa Tyr Leu Asn Leu Val Thr Arg Gln Arg Tyr
1               5                   10                  15

<210> SEQ ID NO 45
<211> LENGTH: 13
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is 3,4,5-trifluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 45

Leu Arg Xaa Tyr Leu Asn Leu Val Thr Arg Gln Arg Tyr
1               5                   10

<210> SEQ ID NO 46
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: Xaa is 3,4,5-trifluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 46

Ile Lys Pro Glu Ala Pro Gly Glu Asp Ala Ser Pro Glu Glu Leu Asn
1               5                   10                  15

Arg Tyr Tyr Ala Ser Leu Arg Xaa Tyr Leu Asn Leu Val Thr Arg Gln
            20                  25                  30

Arg Tyr

<210> SEQ ID NO 47
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (4)..(4)
<223> OTHER INFORMATION: Xaa is 3,4,5-trifluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 47

Leu Arg His Xaa Leu Asn Leu Val Thr Arg Gln Arg Tyr
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (15)..(15)
<223> OTHER INFORMATION: Xaa is 3,4,5-trifluorophenylalanine
<220> FEATURE:
<221> NAME/KEY: MOD_RES
<222> LOCATION: (15)..(15)
<223> OTHER INFORMATION: C-Terminal AMIDATION

<400> SEQUENCE: 48

Ala Ser Leu Arg His Tyr Leu Asn Leu Val Thr Arg Gln Arg Xaa
1               5                   10                  15

<210> SEQ ID NO 49
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (13)..(13)
<223> OTHER INFORMATION: Xaa is 3,4,5-trifluorophenylalanine
<220> FEATURE:
<221> NAME/KEY: MOD_RES
<222> LOCATION: (13)..(13)
<223> OTHER INFORMATION: C-Terminal AMIDATION

<400> SEQUENCE: 49

Leu Arg His Tyr Leu Asn Leu Val Thr Arg Gln Arg Xaa
1               5                   10

<210> SEQ ID NO 50
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa is 3,4,5-trifluorophenylalanine
<220> FEATURE:
<221> NAME/KEY: MOD_RES
<222> LOCATION: (34)..(34)
<223> OTHER INFORMATION: C-Terminal AMIDATION

<400> SEQUENCE: 50

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Xaa

<210> SEQ ID NO 51
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
```

```
<220> FEATURE:
<221> NAME/KEY: MISC_FEATURE
<222> LOCATION: (8)..(8)
<223> OTHER INFORMATION: Xaa is 1-amino-1-cyclopentanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 51

Leu Arg His Tyr Leu Asn Leu Xaa Thr Arg Gln Arg Tyr
1               5                   10

<210> SEQ ID NO 52
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (8)..(8)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 52

Ile Lys Pro Glu Ala Pro Gly Xaa Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 53
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 53

Ile Lys Pro Glu Ala Pro Gly Glu Xaa Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 54
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Xaa is 1-amino-1-cyclohexanecarboxylic acid
<220> FEATURE:
<221> NAME/KEY: MOD_RES
```

<222> LOCATION: (34)..(34)
<223> OTHER INFORMATION: C-Terminal AMIDATION

<400> SEQUENCE: 54

Ile Lys Pro Glu Ala Pro Gly Glu Asp Xaa Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 55
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 55

Ile Lys Pro Glu Ala Pro Gly Glu Asp Ala Xaa Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 56
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (13)..(13)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 56

Ile Lys Pro Glu Ala Pro Gly Glu Asp Ala Ser Pro Xaa Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 57
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (14)..(14)
<223> OTHER INFORMATION: Xaa is 1-amino-1-cyclohexanecarboxylic acid
<220> FEATURE:
<221> NAME/KEY: MOD_RES
<222> LOCATION: (34)..(34)

<223> OTHER INFORMATION: C-Terminal AMIDATION

<400> SEQUENCE: 57

Ile Lys Pro Glu Ala Pro Gly Glu Asp Ala Ser Pro Glu Xaa Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 58
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (15)..(15)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 58

Ile Lys Pro Glu Ala Pro Gly Glu Asp Ala Ser Pro Glu Glu Xaa Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 59
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 59

Ile Lys Pro Glu Ala Pro Gly Glu Asp Ala Ser Pro Glu Glu Leu Xaa
1               5                   10                  15

Arg Tyr Tyr Ala Ser Leu Arg His Tyr Leu Asn Leu Val Thr Arg Gln
            20                  25                  30

Arg Tyr

<210> SEQ ID NO 60
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(18)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 60

Ile Lys Pro Glu Ala Pro Gly Glu Asp Ala Ser Pro Glu Glu Leu Asn
1               5                   10                  15

Arg Xaa Tyr Ala Ser Leu Arg His Tyr Leu Asn Leu Val Thr Arg Gln
            20                  25                  30

Arg Tyr

<210> SEQ ID NO 61
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (19)..(19)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 61

Ile Lys Pro Glu Ala Pro Gly Glu Asp Ala Ser Pro Glu Glu Leu Asn
1               5                   10                  15

Arg Tyr Xaa Ala Ser Leu Arg His Tyr Leu Asn Leu Val Thr Arg Gln
            20                  25                  30

Arg Tyr

<210> SEQ ID NO 62
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 1-amino-1-cyclohexanecarboxylic acid
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MOD_RES
<222> LOCATION: (15)..(15)
<223> OTHER INFORMATION: C-Terminal AMIDATION

<400> SEQUENCE: 62

Xaa Ser Leu Arg His Tyr Leu Asn Leu Val Thr Arg Gln Arg Tyr
1               5                   10                  15

<210> SEQ ID NO 63
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (20)..(20)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 63

```
Ile Lys Pro Glu Ala Pro Gly Glu Asp Ala Ser Pro Glu Glu Leu Asn
1               5                   10                  15

Arg Tyr Tyr Xaa Ser Leu Arg His Tyr Leu Asn Leu Val Thr Arg Gln
            20                  25                  30

Arg Tyr

<210> SEQ ID NO 64
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 1-amino-1-cyclohexanecarboxylic acid
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MOD_RES
<222> LOCATION: (13)..(13)
<223> OTHER INFORMATION: C-Terminal AMIDATION

<400> SEQUENCE: 64

Xaa Arg His Tyr Leu Asn Leu Val Thr Arg Gln Arg Tyr
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (6)..(6)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 65

Ala Ser Leu Arg His Xaa Leu Asn Leu Val Thr Arg Gln Arg Tyr
1               5                   10                  15

<210> SEQ ID NO 66
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (4)..(4)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION
```

```
<400> SEQUENCE: 66

Leu Arg His Xaa Leu Asn Leu Val Thr Arg Gln Arg Tyr
1               5                   10

<210> SEQ ID NO 67
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (25)..(25)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 67

Ile Lys Pro Glu Ala Pro Gly Glu Asp Ala Ser Pro Glu Glu Leu Asn
1               5                   10                  15

Arg Tyr Tyr Ala Ser Leu Arg His Xaa Leu Asn Leu Val Thr Arg Gln
            20                  25                  30

Arg Tyr

<210> SEQ ID NO 68
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 68

Leu Arg His Tyr Xaa Asn Leu Val Thr Arg Gln Arg Tyr
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (8)..(8)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 69

Ala Ser Leu Arg His Tyr Leu Xaa Leu Val Thr Arg Gln Arg Tyr
```

<210> SEQ ID NO 70
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (6)..(6)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 70

Leu Arg His Tyr Leu Xaa Leu Val Thr Arg Gln Arg Tyr
1               5                   10

<210> SEQ ID NO 71
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (27)..(27)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 71

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Xaa Leu Val Thr Arg Gln
            20                  25                  30

Arg Tyr

<210> SEQ ID NO 72
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 72

Xaa Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 73
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (7)..(7)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 73

Leu Arg His Tyr Leu Asn Xaa Val Thr Arg Gln Arg Tyr
1               5                   10

<210> SEQ ID NO 74
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (29)..(29)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 74

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Xaa Thr Arg Gln
            20                  25                  30

Arg Tyr

<210> SEQ ID NO 75
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (11)..(11)
<223> OTHER INFORMATION: Xaa is 1-amino-1-cyclohexanecarboxylic acid
<220> FEATURE:
<221> NAME/KEY: MOD_RES
<222> LOCATION: (15)..(15)
<223> OTHER INFORMATION: C-Terminal AMIDATION

<400> SEQUENCE: 75

Ala Ser Leu Arg His Tyr Leu Asn Leu Val Xaa Arg Gln Arg Tyr
1               5                   10                  15

<210> SEQ ID NO 76
<211> LENGTH: 13

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (9)..(9)
<223> OTHER INFORMATION: Xaa is 1-amino-1-cyclohexanecarboxylic acid
<220> FEATURE:
<221> NAME/KEY: MOD_RES
<222> LOCATION: (13)..(13)
<223> OTHER INFORMATION: C-Terminal AMIDATION

<400> SEQUENCE: 76

Leu Arg His Tyr Leu Asn Leu Val Xaa Arg Gln Arg Tyr
1               5                   10

<210> SEQ ID NO 77
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (30)..(30)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 77

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Xaa Arg Gln
            20                  25                  30

Arg Tyr

<210> SEQ ID NO 78
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 78

Ile Lys Pro Xaa Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 79
<211> LENGTH: 34
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 79

Ile Lys Pro Glu Xaa Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 80
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is 1-amino-1-cyclohexanecarboxylic acid
<220> FEATURE:
<221> NAME/KEY: MOD_RES
<222> LOCATION: (34)..(34)
<223> OTHER INFORMATION: C-Terminal AMIDATION

<400> SEQUENCE: 80

Ile Lys Pro Glu Ala Pro Xaa Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 81
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Xaa is 4-amino-4-carboxytetrahydropyran
<220> FEATURE:
<221> NAME/KEY: MOD_RES
<222> LOCATION: (34)..(34)
<223> OTHER INFORMATION: C-Terminal AMIDATION

<400> SEQUENCE: 81

Ile Lys Pro Glu Ala Pro Gly Glu Asp Xaa Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 82
<211> LENGTH: 34
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (11)..(11)
<223> OTHER INFORMATION: Xaa is 4-amino-4-carboxytetrahydropyran
<220> FEATURE:
<221> NAME/KEY: MOD_RES
<222> LOCATION: (34)..(34)
<223> OTHER INFORMATION: C-Terminal AMIDATION

<400> SEQUENCE: 82

Ile Lys Pro Glu Ala Pro Gly Glu Asp Ala Xaa Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 83
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (2)..(2)
<223> OTHER INFORMATION: Xaa is 4-amino-4-carboxytetrahydropyran
<220> FEATURE:
<221> NAME/KEY: MOD_RES
<222> LOCATION: (15)..(15)
<223> OTHER INFORMATION: C-Terminal AMIDATION

<400> SEQUENCE: 83

Ala Xaa Leu Arg His Tyr Leu Asn Leu Val Thr Arg Gln Arg Tyr
1               5                   10                  15

<210> SEQ ID NO 84
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (21)..(21)
<223> OTHER INFORMATION: Xaa is 4-amino-4-carboxytetrahydropyran
<220> FEATURE:
<221> NAME/KEY: MOD_RES
<222> LOCATION: (34)..(34)
<223> OTHER INFORMATION: C-Terminal AMIDATION

<400> SEQUENCE: 84

Ile Lys Pro Glu Ala Pro Gly Glu Asp Ala Ser Pro Glu Glu Leu Asn
1               5                   10                  15

Arg Tyr Tyr Ala Xaa Leu Arg His Tyr Leu Asn Leu Val Thr Arg Gln
            20                  25                  30

Arg Tyr

<210> SEQ ID NO 85
<211> LENGTH: 15
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (11)..(11)
<223> OTHER INFORMATION: Xaa is 4-amino-4-carboxytetrahydropyran
<220> FEATURE:
<221> NAME/KEY: MOD_RES
<222> LOCATION: (15)..(15)
<223> OTHER INFORMATION: N-Terminal AMIDATION

<400> SEQUENCE: 85

Ala Ser Leu Arg His Tyr Leu Asn Leu Val Xaa Arg Gln Arg Tyr
1               5                   10                  15

<210> SEQ ID NO 86
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (9)..(9)
<223> OTHER INFORMATION: Xaa is 4-amino-4-carboxytetrahydropyran
<220> FEATURE:
<221> NAME/KEY: MOD_RES
<222> LOCATION: (13)..(13)
<223> OTHER INFORMATION: C-Terminal AMIDATION

<400> SEQUENCE: 86

Leu Arg His Tyr Leu Asn Leu Val Xaa Arg Gln Arg Tyr
1               5                   10

<210> SEQ ID NO 87
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (30)..(30)
<223> OTHER INFORMATION: Xaa is 4-amino-4-carboxytetrahydropyran
<220> FEATURE:
<221> NAME/KEY: MOD_RES
<222> LOCATION: (34)..(34)
<223> OTHER INFORMATION: C-Terminal AMIDATION

<400> SEQUENCE: 87

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Xaa Arg Gln
            20                  25                  30

Arg Tyr

<210> SEQ ID NO 88
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa is 4-amino-4-carboxytetrahydropyran
```

```
<220> FEATURE:
<221> NAME/KEY: MOD_RES
<222> LOCATION: (34)..(34)
<223> OTHER INFORMATION: C-Terminal AMIDATION

<400> SEQUENCE: 88

Ile Lys Pro Glu Xaa Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 89
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is alpha-aminoisobutyric acid
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MOD_RES
<222> LOCATION: (15)..(15)
<223> OTHER INFORMATION: C-Terminal AMIDATION

<400> SEQUENCE: 89

Xaa Ser Leu Arg His Tyr Leu Asn Leu Val Thr Arg Gln Arg Tyr
1               5                   10                  15

<210> SEQ ID NO 90
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (17)..(17)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 90

Ile Lys Pro Glu Ala Pro Gly Glu Asp Ala Ser Pro Glu Glu Leu Asn
1               5                   10                  15

Xaa Tyr Tyr Ala Ser Leu Arg His Tyr Leu Asn Leu Val Thr Arg Gln
            20                  25                  30

Arg Tyr

<210> SEQ ID NO 91
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
```

```
<222> LOCATION: (4)..(4)
<223> OTHER INFORMATION: Xaa is Apc as defined in the specification
<220> FEATURE:
<221> NAME/KEY: MOD_RES
<222> LOCATION: (15)..(15)
<223> OTHER INFORMATION: C-Terminal AMIDATION

<400> SEQUENCE: 91

Ala Ser Leu Xaa His Tyr Leu Asn Leu Val Thr Arg Gln Arg Tyr
1               5                   10                  15

<210> SEQ ID NO 92
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (2)..(2)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 92

Leu Xaa His Tyr Leu Asn Leu Val Thr Arg Gln Arg Tyr
1               5                   10

<210> SEQ ID NO 93
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (23)..(23)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 93

Ile Lys Pro Glu Ala Pro Gly Glu Asp Ala Ser Pro Glu Glu Leu Asn
1               5                   10                  15

Arg Tyr Tyr Ala Ser Leu Xaa His Tyr Leu Asn Leu Val Thr Arg Gln
            20                  25                  30

Arg Tyr

<210> SEQ ID NO 94
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (5)..(5)
<223> OTHER INFORMATION: Xaa is Apc as defined in the specification
<220> FEATURE:
```

```
<221> NAME/KEY: MOD_RES
<222> LOCATION: (15)..(15)
<223> OTHER INFORMATION: C-Terminal AMIDATION

<400> SEQUENCE: 94

Ala Ser Leu Arg Xaa Tyr Leu Asn Leu Val Thr Arg Gln Arg Tyr
1               5                   10                  15

<210> SEQ ID NO 95
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (3)..(3)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 95

Leu Arg Xaa Tyr Leu Asn Leu Val Thr Arg Gln Arg Tyr
1               5                   10

<210> SEQ ID NO 96
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(24)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 96

Ile Lys Pro Glu Ala Pro Gly Glu Asp Ala Ser Pro Glu Glu Leu Asn
1               5                   10                  15

Arg Tyr Tyr Ala Ser Leu Arg Xaa Tyr Leu Asn Leu Val Thr Arg Gln
            20                  25                  30

Arg Tyr

<210> SEQ ID NO 97
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (12)..(12)
<223> OTHER INFORMATION: Xaa is Apc as defined in the specification
<220> FEATURE:
<221> NAME/KEY: MOD_RES
<222> LOCATION: (15)..(15)
<223> OTHER INFORMATION: C-Terminal AMIDATION
```

<400> SEQUENCE: 97

Ala Ser Leu Arg His Tyr Leu Asn Leu Val Thr Xaa Gln Arg Tyr
1               5                   10                  15

<210> SEQ ID NO 98
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (10)..(10)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 98

Leu Arg His Tyr Leu Asn Leu Val Thr Xaa Gln Arg Tyr
1               5                   10

<210> SEQ ID NO 99
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (31)..(31)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 99

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Xaa Gln
            20                  25                  30

Arg Tyr

<210> SEQ ID NO 100
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (13)..(13)
<223> OTHER INFORMATION: Xaa is Apc as defined in the specification
<220> FEATURE:
<221> NAME/KEY: MOD_RES
<222> LOCATION: (15)..(15)
<223> OTHER INFORMATION: C-Terminal AMIDATION

<400> SEQUENCE: 100

```
Ala Ser Leu Arg His Tyr Leu Asn Leu Val Thr Arg Xaa Arg Tyr
1               5                   10                  15
```

<210> SEQ ID NO 101
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (11)..(11)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 101

```
Leu Arg His Tyr Leu Asn Leu Val Thr Arg Xaa Arg Tyr
1               5                   10
```

<210> SEQ ID NO 102
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (32)..(32)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 102

```
Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Xaa
            20                  25                  30

Arg Tyr
```

<210> SEQ ID NO 103
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (14)..(14)
<223> OTHER INFORMATION: Xaa is Apc as defined in the specification
<220> FEATURE:
<221> NAME/KEY: MOD_RES
<222> LOCATION: (15)..(15)
<223> OTHER INFORMATION: C-Terminal AMIDATION

<400> SEQUENCE: 103

```
Ala Ser Leu Arg His Tyr Leu Asn Leu Val Thr Arg Gln Xaa Tyr
1               5                   10                  15
```

```
<210> SEQ ID NO 104
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (12)..(12)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 104

Leu Arg His Tyr Leu Asn Leu Val Thr Arg Gln Xaa Tyr
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (15)..(15)
<223> OTHER INFORMATION: Xaa is Apc as defined in the specification
<220> FEATURE:
<221> NAME/KEY: MOD_RES
<222> LOCATION: (15)..(15)
<223> OTHER INFORMATION: C-Terminal AMIDATION

<400> SEQUENCE: 105

Ala Ser Leu Arg His Tyr Leu Asn Leu Val Thr Arg Gln Arg Xaa
1               5                   10                  15

<210> SEQ ID NO 106
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-Terminal ACETYLATION
<220> FEATURE:
<221> NAME/KEY: MISC_FEATURE
<222> LOCATION: (13)..(13)
<223> OTHER INFORMATION: Xaa is Apc as defined in the specification
<220> FEATURE:
<221> NAME/KEY: MOD_RES
<222> LOCATION: (13)..(13)
<223> OTHER INFORMATION: C-Terminal AMIDATION

<400> SEQUENCE: 106

Leu Arg His Tyr Leu Asn Leu Val Thr Arg Gln Arg Xaa
1               5                   10

<210> SEQ ID NO 107
<211> LENGTH: 34
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 107

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Xaa

<210> SEQ ID NO 108
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is Apc as defined in the specification
<220> FEATURE:
<221> NAME/KEY: MOD_RES
<222> LOCATION: (34)..(34)
<223> OTHER INFORMATION: C-Terminal AMIDATION

<400> SEQUENCE: 108

Ile Xaa Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

PEPTIDE YY ANALOGS

This application is a United States national stage filing under 35 U.S.C. §371 of international (PCT) application no. PCT/US2004/000892, filed Jan. 13, 2004, and designating the U.S., which claims priority to U.S. provisional application 60/440,812 filed Jan 17, 2003.

FIELD OF THE INVENTION

This invention relates to peptides which are useful as therapeutic agents in the treatment of feeding and gastroenterological conditions and disorders.

BACKGROUND OF THE INVENTION

Peptide YY (PYY) is a 36-residue peptide amide isolated originally from porcine intestine, and localized in the endocrine cells of the gastrointestinal tract and pancreas (Tatemoto et al. Proc. Natl. Acad. Sci. 79:2514, 1982). PYY shares a number of central and peripheral regulatory roles with its homologous peptide Neuropeptide Y (NPY), which was originally isolated from porcine brain (Tatemoto, Proc. Natl. Acad. Sci. 79:5485, 1982). PYY is localized in intestinal cells; NPY, in contrast, is present in the submucous and myenteric neurons which innervate the mucosal and smooth muscle layers, respectively (Ekblad et al. Neuroscience 20:169, 1987). Both PYY and NPY are believed to inhibit gut motility and blood flow (Laburthe, Trends Endocrinol. Metab. 1:168, 1990), and they are also thought to attenuate basal (Cox et al. Br. J Pharmacol. 101:247, 1990; Cox et al. J. Physiol. 398:65, 1988; Cox et al. Peptides 12:323, 1991; Friel et al. Br. J. Pharmacol. 88:425, 1986) and secretagogue-induced intestinal secretion in rats (Lundberg et al. Proc. Natl. Acad. Sci USA 79:4471, 1982; Playford et al. Lancet 335: 1555, 1990) and humans (Playford et al., supra), as well as stimulate net absorption (MacFadyen et al. Neuropeptides 7:219, 1986). Elevated plasma PYY levels have been reported in individuals suffering from several conditions that cause diarrhea (Adrian et al. Gastroenterology 89:1070, 1985). Taken together, these observations suggest that PYY and NPY are released into the circulation after a meal (Adrian et al. Gastroenterology 89:1070, 1985; Balasubramaniam et al. Neuropeptides 14:209, 1989), and, thus, may play a physiological role in regulating intestinal secretion and absorption, serving as natural inhibitors of diarrhea.

A high affinity PYY receptor system which exhibits a slightly higher affinity for PYY than NPY has been characterized in rat intestinal epithelia (Laburthe et al. Endocrinology118:1910, 1986; Laburthe, Trends Endocrinol. Metab. supra) and shown to be negatively coupled to adenylate cyclase (Servin et al. Endocrinology 124:692, 1989). Consistently, PYY exhibited greater antisecretory potency than NPY in voltage clamped preparations of rat small intestine (Cox et al. J. Physiol. supra), while C-terminal fragments of NPY were found to be less effective in their antisecretory potency than PYY (Cox et al. Br. J. Pharmacol. supra). Structure-activity studies using several partial sequences have led to the identification of PYY(22-36) as the active site for interacting with intestinal PYY receptors (Balasubramaniam et al. Pept. Res. 1:32, 1988). PYY[3-36] is reportedly a selective ligand at the Y2 and Y5 receptors, which appear pharmacologically unique in preferring N-terminally truncated (i.e. C-terminal fragments of) NPY analogs.

PYY has been implicated in a number of physiological activities including nutrient uptake (see, e.g., Bilcheik et al. Digestive Disease Week 506:623, 1993), cell proliferation (see, e.g., Laburthe, Trends Endocrinol. Metab. 1:168, 1990; Voisin et al. J. Biol. Chem, 1993), lipolysis (see, e.g., Valet et al., J. Clin. Invest. 85:291, 1990), and vasoconstriction (see, e.g., Lundberg et al., Proc. Natl. Acad. Sci., USA 79:4471, 1982). Recently it has been suggested that infusion of normal postprandial concentrations of PYY(3-36) significantly reduces appetite and food intake in humans (see Batterham et al., Nature 418:656-654, 2002; Batterham et al., N Engl J Med. 349:941, 2003).

Peripheral administration of PYY reportedly reduces gastric acid secretion, gastric motility, exocrine pancreatic secretion (Yoshinaga, Mochizuki et al. Am J Physiol 263: G695-701, 1992) (Guan, Maouyo et al. Endocrinology 128: 911-6, 1991) (Pappas, Debas et al. Gastroenterology 91: 1386-9, 1986), gallbladder contraction and intestinal motility (Savage, Adrian et al. Gut 28: 166-70, 1987). The effects of central injection of PYY on gastric emptying, gastric motility and gastric acid secretion, as seen after direct injection in or around the hindbrain/brainstem (Chen and Rogers. Am J Physiol 269: R787-R792, 1995) (Chen, Rogers et al. Regul Pept 61: 95-98, 1996) (Yang and Tache. Am J Physiol 268: G943-8, 1995) (Chen, Stephens et al. Neurogastroenterol Motil 9: 109-116, 1997), may differ from those effects observed after peripheral injection. For example, centrally administered PYY had some effects opposite to those described herein for peripherally injected PYY[3-36] in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley, Levine et al. Brain Res 341: 200-203, 1985) (Corp, Melville et al. Am J Physiol 259: R317-23, 1990).

Pharmacological studies and cloning efforts have revealed a number of seven transmembrane receptors for the PP family of peptides, and these receptors have been assigned the names Y1 through Y6 (and a putative PYY-preferring receptor or Y7). Typical signaling responses of these receptors are similar to those of other $G_i/G_0$-coupled receptors, namely inhibition of adenylate cyclase. It is apparent that there is a clustering of amino acid sequence similarity between Y1, Y4 and Y6 receptors, while Y2 and Y5 define other families. Other binding sites have been identified by the rank order of potency of various peptides. The NPY-preferring receptor has been termed Y3, and PYY-preferring receptors have also been shown to exist (putative Y7) (See Michel, Beck-Sickinger et al. Pharmacol Rev 50:143-50, 1998; and Gehlert, D. R. Proc Soc Exp Biol Med 218: 7-22, 1998).

The Y5 and Y1 receptors have been suggested as the primary mediators of the food intake response (Marsh, Hollopeter et al. Nat Med 4: 718-21, 1998) (Kanatani, A., Mashiko, S., Murai, N., Sugimoto, N., Ito, J., Fukuroda, T., Fukami, T., Morin, N., MacNeil, D. J., Van der Ploeg, L. H., Saga, Y., Nishimura, S., and Ihara, M. Endocrinology 141: 1011-6, 2000). The prevalent idea has been that endogenous NPY, via these receptors, increases feeding behavior. Some proposed therapies for obesity have been directed toward antagonism of NPY receptors, while therapies for treating anorexia have been directed toward agonists of this ligand family (see, e.g., U.S. Pat. Nos. 5,939,462; 6,013,622; and 4,891,357). In general, PYY and NPY are reported to be equipotent and equally effective in all Y1, Y5 (and Y2) receptor assays studied (Gehlert, D. R. Proc Soc Exp Biol Med 218: 7-22, 1998). The main characteristic of putative Y3 receptors is that they recognize NPY, while PYY is at least an order of magnitude less potent.

The Y3 receptor represents the only binding site/receptor shown to have a preference for NPY.

There is an additional binding site/receptor which shows preference for PYYs, termed PYY-preferring receptor. Different rank orders of binding to this receptor, or class of receptors, have been reported, suggesting that there may be more than one receptor in this family. In most cases it has been applied to describe a receptor where PYY was three to five times more potent than NPY. For purposes of this disclosure, reference to pharmacology of a PYY-preferring receptor means a receptor having any degree of preference for PYY over NPY.

Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. (see, e.g., Kopelman, Nature 404: 635-43, 2000). It reduces life-span and carries a serious risk of co-morbidities above, as well disorders such as infections, varicose veins, acanthosis nigricans, eczema, exercise intolerance, insulin resistance, hypertension, hypercholesterolemia, cholelithiasis, orthopedic injury, and thromboembolic disease (Rissanen, Heliovaara et al. BMJ 301: 8357, 1990). Obesity is also a risk factor for the group of conditions called insulin resistance syndrome, or "Syndrome X." The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. Thus there remains a need for therapeutic drugs useful in weight reduction of obese persons.

SUMMARY OF THE INVENTION

Peripheral administration of PYY and PYY agonists reduces nutrient availability and is useful in the treatment of obesity and related disorders. PYY and PYY agonist compositions and uses thereof are disclosed herein to modulate nutrient availability in a patient for treating metabolic disorders which may be benefited by a reduction in nutrient availability. These methods will be useful in the treatment of, for example, obesity, diabetes, including but not limited to type 2 or non-insulin dependent diabetes, eating disorders, insulin-resistance syndrome, and cardiovascular disease.

Unless otherwise indicated the term "PYY" refers to a Peptide YY polypeptide obtained or derived from any species. Thus, the term "PYY" includes both the human full length, 36 amino acid peptide as set forth in SEQ ID NO: 1, and species variations of PYY, including e.g., murine, hamster, chicken, bovine, rat, and dog PYY. By "PYY agonist" is meant any compound which elicits one of more of the effects elicited by PYY in vivo or in vitro. For example, a PYY agonist of the invention may reduce nutrient availability, for example, by augmenting food intake, gastric emptying, pancreatic secretion, or weight loss, and bind in a PYY receptor assay, or in a competitive binding assay with labeled PYY or PYY[3-36] from certain tissues having an abundance of Y receptors, including e.g., area postrema, wherein the PYY agonist is not pancreatic polypeptide. Preferably, PYY agonists would bind in such assays with an affinity of greater than about 1 μM, more preferably with an affinity of greater than about 10 nM, more preferably still with an affinity of greater than about 1 nM. Also preferably, analogs of the invention comprise compounds according to formula (I) that bind in such assays with an affinity of greater than about 1 μM, more preferably with an affinity of greater than about 10 nM, more preferably still with an affinity of greater than about 1 nM.

By "condition or disorder which can be alleviated by reducing caloric (or nutrient) availability" is meant any condition or disorder in a subject that is either caused by, complicated by, or aggravated by a relatively high nutrient availability, or that can be alleviated by reducing nutrient availability, for example by decreasing food intake. Such conditions or disorders include, but are not limited to, obesity, diabetes, including type-2 diabetes, eating disorders, and insulin-resistance syndromes.

In one aspect, the invention provides a method of treating obesity in an obese or overweight subject by administering a therapeutically effective amount of a PYY agonist of the invention. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects, the invention features methods of reducing food intake, treating diabetes mellitus, and improving lipid profile (including reducing LDL cholesterol and triglyceride levels and/or changing HDL cholesterol levels) comprising administering to a subject a therapeutically effective amount of a compound according to formula (I). In a preferred embodiment, a method of the invention is used to treat a condition or disorder which can be alleviated by reducing nutrient availability in a subject in need thereof, comprising administering to said subject a therapeutically effective amount of a PYY agonist of the invention. Such conditions and disorders include, but are not limited to, hypertension, dyslipidemia, cardiovascular disease, eating disorders, insulin-resistance, obesity, and diabetes mellitus of any kind.

The amino acid sequences for human and for rat PYY are as follows human: YPIKP EAPGE DASPE ELNRY YASLR HYLNL VTRQR Y (SEQ ID NO:1)

rat: YPAKP EAPGE DASPE ELSRY YASLR HYLNL VTRQR Y (SEQ ID NO:2)

Further PYY amino acid sequences are well known, including, e.g., porcine, hamster, canine, bovine, and avian (e.g, chicken).

The following patents and patent publications, the disclosure of each of which is incorporated herein by reference in its entirety, disclose certain PYY analogs and uses thereof: EP0692971, EP0732875, EP0746332, EP0802972, EP1007073, EP1015007, US2002/103123, US2002/141985, U.S. Pat. Nos. 5,516,653, 5,545,549, 5,574,010, 5,602,024, 5,604,203 , 5,912,227, 5,916,869, 5,968,819, 5,976,814, 5,989,834, 5,989,920, 6,046,167, 6,087,154, 6,242,251, 6,316,203, 6,355,478, WO01/54486, WO02/47712, WO93/24515, WO94/22467, WO95/17906, WO95/21245, WO96/14854, WO96/16542, WO96/22783, WO97/46250, WO97/48406, and WO98/20885.

Notwithstanding the foregoing there remains a continuing need for PYY analogs having improved PYY potency and/or selectivity and/or in vitro or in vivo characteristics.

SUMMARY OF THE INVENTION

In one aspect, the present invention is directed to the peptides formula (I):

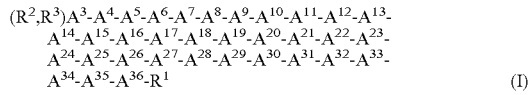

$$(R^2,R^3)A^3\text{-}A^4\text{-}A^5\text{-}A^6\text{-}A^7\text{-}A^8\text{-}A^9\text{-}A^{10}\text{-}A^{11}\text{-}A^{12}\text{-}A^{13}\text{-}$$
$$A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}A^{23}\text{-}$$
$$A^{24}\text{-}A^{25}\text{-}A^{26}\text{-}A^{27}\text{-}A^{28}\text{-}A^{29}\text{-}A^{30}\text{-}A^{31}\text{-}A^{32}\text{-}A^{33}\text{-}$$
$$A^{34}\text{-}A^{35}\text{-}A^{36}\text{-}R^1 \qquad (I)$$

wherein:

$A^3$ is Acc, Act, or Aib, or a D- or L-amino acid selected from the list of amino acids consisting of Ile, Leu, Nle, Tle, hLeu, Cha, Val, Ala, Nva, and Abu, or the N-methylated variant of Acc, Act, or Aib, or of said D- or L-amino acid, or is deleted;

$A^4$ is Aib, Acc, or Apc, or a D- or L-amino acid selected from the list of amino acids consisting of Lys, Arg, hArg, Orn, Dab, Dap, and HN—CH((CH$_2$)$_n$—N(R$^4$R$^5$))—C(O), or the N-methylated variant of Aib, Acc, or Apc, or of said D- or L-amino acid, or is deleted;

$A^5$ is a D- or L-amino acid selected from the list of amino acids consisting of Pro, Thz, Dmt, Dhp, Ktp, 4Hyp, 3Hyp, Pip, Tic, Inc and Oic, or the N-methylated variant of Inc or of said D- or L-amino acid, or is deleted;

$A^6$ is Acc or Aib, or a D- or L-amino acid selected from the list of amino acids consisting of Glu, Asp, Gln, Asn, Lys, Arg, Orn, Dab, Dap, and hArg, or the N-methylated variant of Acc or Aib, or of said D- or L-amino acid, or is deleted;

$A^7$ is Acc, Act, Aib, Apc, or Gly, or a D- or L-amino acid selected from the list of amino acids consisting of Ala, Abu, Val, and Nva, or the N-methylated variant of Acc, Act, Aib, Apc, or Gly, or of said D- or L-amino acid, or is deleted;

$A^8$ is a D- or L-amino acid selected from the list of amino acids consisting of Pro, Thz, Dmt, Dhp, Ktp, 4Hyp, 3Hyp, Pip, Tic, Inc and Oic, or the N-methylated variant of Inc or of said D- or L-amino acid, or is deleted;

$A^9$ is Acc, Aib, or Gly, or D- or L-Ala, or the N-methylated variant of Acc, Aib, Gly, or D- or L-Ala, or is deleted;

$A^{10}$ is Acc or Aib, or a D- or L-amino acid selected from the list of amino acids consisting of Glu, Asp, Gln, and Asn, or the N-methylated variant of Acc or Aib, or of said D- or L-amino acid, or is deleted;

$A^{11}$ is Acc or Aib, or a D- or L-amino acid selected from the list of amino acids consisting of Asp, Glu, Gln, and Asn, or the N-methylated variant of Acc or Aib, or of said D- or L-amino acid, or is deleted;

$A^{12}$ is Acc, Act, Aib, Apc, or Gly, or a D- or L-amino acid selected from the list of amino acids consisting of Ala, Abu, Val, and Nva, or the N-methylated variant of Acc, Act, Aib, Apc, or Gly, or of said D- or L-amino acid, or is deleted;

$A^{13}$ is Acc, Aib, or Act, or a D- or L-amino acid selected from the list of amino acids consisting of Ser, Thr, Ala, Abu, and Val, or the N-methylated variant of Acc, Aib, or Act, or of said D- or L-amino acid, or is deleted;

$A^{14}$ is a D- or L-amino acid selected from the list of amino acids consisting of Pro, Thz, Dmt, Dhp, Ktp, 4Hyp, 3Hyp, Pip, Tic, Inc and Oic, or the N-methylated variant of Inc or of said D- or L-amino acid, or is deleted;

$A^{15}$ is Acc or Aib, or a D- or L-amino acid selected from the list of amino acids consisting of Glu, Asp, Gln, and Asn, or the N-methylated variant of Acc or Aib, or of said D- or L-amino acid, or is deleted;

$A^{16}$ is Acc or Aib, or a D- or L-amino acid selected from the list of amino acids consisting of Glu, Asp, Gln, and Asn, or the N-methylated variant of Acc or Aib, or of said D- or L-amino acid, or is deleted;

$A^{17}$ is Acc or Aib, or a D- or L-amino acid selected from the list of amino acids consisting of Leu, Ile, Nle, Tle, hLeu, Cha, Val, Ala, Nva, Abu, and Phe, or the N-methylated variant of Acc or Aib, or of said D- or L-amino acid, or is deleted;

$A^{18}$ is Acc or Aib, or a D- or L-amino acid selected from the list of amino acids consisting of Asn, Gln, Glu, and Asp, or the N-methylated variant of Acc or Aib, or of said D- or L-amino acid, or is deleted;

$A^{19}$ is Acc, Aib, or Apc, or a D- or L-amino acid selected from the list of amino acids consisting of Arg, hArg, Lys, Orn, Dab, Dap, and HN—CH((CH$_2$)$_n$—N(R$^4$R$^5$))—C(O), or the N-methylated variant of Acc, Aib, or Apc, or of said D- or L-amino acid, or is deleted;

$A^{20}$ is Acc or Aic, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and (X$^1$, X$^2$,X$^3$ X$^4$,X$^5$)Phe, or the N-methylated variant of Acc or Aic, or of said D- or L-amino acid, or is deleted;

$A^{21}$ is Acc or Aic, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and (X$^1$, X$^2$,X$^3$,X$^4$,X$^5$)Phe, or the N-methylated variant of Acc or Aic, or of said D- or L-amino acid, or is deleted;

$A^{22}$ is Acc, Act, Aib, Apc, or Gly, or a D- or L-amino acid selected from the list of amino acids consisting of Ala, Aib, Abu, Val, and Nva, or the N-methylated variant of Ala, Acc, Act, Aib, Apc, or Gly, or of said D- or L-amino acid, or is deleted;

$A^{23}$ is Acc, Act, or Aib, or a D- or L-amino acid selected from the list of amino acids consisting of Trp, Ser, Thr, Ala, Abu, and Val, or the N-methylated variant of Acc, Act, or Aib, or of said D- or L-amino acid, or is deleted;

$A^{24}$ is Acc or Aib, or a D- or L-amino acid selected from the list of amino acids consisting of Leu, Ile, Nle, Tle, hLeu, Cha, Val, Ala, Nva, Abu, Trp, and Phe, or the N-methylated variant of Acc or Aib, or of said D- or L-amino acid, or is deleted;

$A^{25}$ is Acc, Aib, or Apc, or a D- or L-amino acid selected from the list of amino acids consisting of Arg, hArg, Lys, Orn, Dab, Dap, Aib, and HN—CH((CH$_2$)$_n$—N(R$^4$R$^5$))—C(O), or the N-methylated variant of Acc, Aib, or Apc, or of said D- or L-amino acid, or is deleted;

$A^{26}$ is Acc, Aib, or Apc, or a D- or L-amino acid selected from the list of amino acids consisting of His, 2Pal, 3Pal, 4Pal, Taz, 2Thi, 3Thi, 2Fua, HN—CH((CH$_2$)$_n$—N(R$^4$R$^5$))—C(O), and (X$^1$,X$^2$,X$^3$,X$^4$,X$^5$-)Phe, or the N-methylated variant of Acc, Aib, or Apc, or of said D- or L-amino acid, or is deleted;

$A^{27}$ is Acc or Aic, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and (X$^1$, X$^2$,X$^3$,X$^4$,X$^5$)Phe, or the N-methylated variant of Acc or Aic or of said D- or L-amino acid;

$A^{28}$ is Acc or Aib, a D- or L-amino acid selected from the list of amino acids consisting of Leu, Ile, Nle, Tle, hLeu, Trp, Cha, Val, Ala, Nva, Abu, and Phe, or the N-methylated variant of Acc or Aib, or of said D- or L-amino acid;

$A^{29}$ is Acc or Aib, or a D- or L-amino acid selected from the list of amino acids consisting of Asn, Gln, Glu, Asp, and Trp, or the N-methylated variant of Acc or Aib, or of said D- or L-amino acid;

$A^{30}$ is Acc or Aib, or a D- or L-amino acid selected from the list of amino acids consisting of Leu, Ile, Nle, Tle, hLeu, Trp, Cha, Val, Ala, Nva, Abu, and Phe or the N-methylated variant of Acc or Aib, or of said D- or L-amino acid;

$A^{31}$ is Acc or Aib, or a D- or L-amino acid selected from the list of amino acids consisting of Val, Leu, Ile, Nle, Tle, hLeu, Cha, Ala, Nva, Abu, Trp, and Phe, or the N-methylated variant of Acc or Aib, or of said D- or L-amino acid;

$A^{32}$ is Acc, Act, or Aib, or a D- or L-amino acid selected from the list of amino acids consisting of Thr, Ser, Ala, Abu, Trp, DTrp, and Val, or the N-methylated variant of Acc, Act, or Aib, or of said D- or L-amino acid;

A33 is Acc, Aib, or Apc, or a D- or L-amino acid selected from the list of amino acids consisting of Arg, hArg, Lys, Orn, Dab, Dap, and HN—CH$((CH_2)_n$—N$(R^4R^5))$—C(O), or the N-rnethylated variant of Acc, Aib, or Apc, or of said D- or L-amino acid;

$A^{34}$ is Acc, Aib, or Apc, or a D- or L-amino acid selected from the list of amino acids consisting of Gln, Asn, Glu, Asp, or the N-methylated variant of Acc, Aib, or Apc, or of said D- or L-amino acid;

$A^{35}$ is Acc, Aib, or Apc, or a D- or L-amino acid selected from the list of amino acids consisting of Arg, hArg, Lys, Orn, Dab, Dap, and HN—CH$((CH_2)_n$—N$(R^4R^5))$—C(O), or the N-methylated variant of Acc, Aib, or Apc, or of said D- or L-amino acid;

$A^{36}$ is Acc, Aic or Apc, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and $(X^1,X^2,X^3,X^4,X^5)$Phe, or the N-methylated variant of Acc, Aic, or Apc, or of said N or L-amino acid;

$R^1$ is OH or $NH_2$, $(C_1-C_{30})$alkoxy, or NH—$X^6$—$CH_2$-$Z^0$, wherein $X^6$ is a $(C_1-C_{12})$hydrocarbon moiety, and $Z^0$ is —H, —OH, —$CO_2$H or —C(O)$NH_2$;

$R^2$ and $R^3$ each is, independently for each occurrence, selected from the group consisting of —H, $(C_1-C_{30})$alkyl, $(C_1-C_{30})$heteroalkyl, $(C_1-C_{30})$acyl, $(C_2-C30)$alkenyl, $(C_2-C_{30})$alkynyl, aryl$(C_1-C_{30})$alkyl, aryl$(C_1-C_{30})$acyl, substituted $(C_1-C_{30})$alkyl, substituted $(C_1-C_{30})$heteroalkyl, substituted $(C_2-C_{30})$acyl, substituted $(C_2-C_{30})$alkenyl, substituted $(C_2-C_{30})$alkynyl, substituted aryl$(C_1-C_{30})$alkyl, and substituted aryl$(C_1-C_{30})$acyl, provided that when $R^2$ is $(C_1-C_{30})$acyl, aryl$(C_1-C_{30})$acyl, substituted $(C_2-C_{30})$acyl, or substituted aryl$(C_1-C_{30})$acyl, then $R^3$ is —H, $(C_1-C_{30})$alkyl, $(C_1-C_{30})$heteroalkyl, $(C_2-C_{30})$alkenyl, $(C_2-C_{30})$alkynyl, aryl$(C_1-C_{30})$alkyl, substituted $(C_1-C_{30})$alkyl, substituted $(C_1-C_{30})$heteroalkyl, substituted $(C_2-C_{30})$alkenyl, substituted $(C_2-C_{30})$alkynyl, or substituted aryl $(C_1-C_{30})$alkyl;

$R^4$ and $R^5$ each is, independently for each occurrence, selected from the group consisting of —H, $(C_1-C_{40})$alkyl, $(C_2-C_{40})$acyl, $(C_1-C_{30})$alkylsulfonyl, and —C(NH)$NH_2$, provided that when $R^4$ is $(C_1-C_{40})$acyl, $(C_1-C_{30})$alkylsulfonyl, or —C(NH)$NH_2$, then $R^5$ is —H or $(C_1-C_{40})$alkyl;

n is, independently for each occurrence, 1, 2, 3, 4 or 5; and $X^1$, $X^2$, $X^3$, $X^4$, and $X^5$ each is, independently for each occurrence, selected from the group consisting of —H, —F, —Cl, —Br, —I, $(C_1-C_{10})$alkyl, substituted $(C_1-C_{10})$alkyl, aryl, substituted aryl, —OH, —$NH_2$, —$NO_2$, and —CN;

provided that:

(a) said peptide comprises at least one amino acid selected from the group consisting of:

(i) Acc at $A^3, A^6, A^7, A^9, A^{10}, A^{11}, A^{12}, A^{15}, A^{16}, A^{17}, A^{18}, A^{20}, A^{21}, A^{22}, A^{24}, A^{27}, A^{28}, A^{29}, A^{30}, A^{31}, A^{32}$, or $A^{34}$;

(ii) Act at $A^3, A^7, A^{12}, A^{13}, A^{22}, A^{23}$, or $A^{32}$;

(iii) Apc at $A^4, A^7, A^{12}, A^{19}, A^{22}, A^{25}, A^{26}, A^{33}, A^{34}, A^{35}$, or $A^{36}$;

(iv) Aib at $A^6, A^7, A^9, A^{10}, A^{11}, A^{12}, A^{13}, A^{15}, A^{16}$; $A^{18}$, $A^{22}, A^{29}$ or $A^{32}$;

(v) Thz, Dmt, Dhp, Ktp, or Tic at $A^5, A^8$, or $A^{14}$;

(vi) (3,4,5-F)Phe or (2,3,4,5,6-F)Phe at $A^{20}, A^{21}, A^{26}, A^{27}$, or $A^{36}$;

(vii) 2Fua at $A^{20}, A^{21} A^{26}$, or $A^{27}$;

(viii) Taz at $A^{20}, A^{21}$, or $A^{26}$; and (ix) 2Pal, 3Pal, 4Pal, 2Thi or 3Thi at $A^{26}$;

(b) if $A^3$-$A^{21}$ are deleted and (i) A22 is Aib or (ii) As is (3,4,5-F)Phe or (2,3,4,5,6-F)Phe, then $A^{27}$ is not 2Thi, Trp, 2Nal, or $(X^1,X^2,X^3,X^4,X^5)$Phe, wherein $X^1$ is p-chloro and $X^2, X^3, X^4$ and $X^5$ each is —H; and (c) each amino acid $A^m$ of formula (I) may be deleted only if $A^{m-1}$ is deleted, wherein m is an integer ranging in value from 4-26, inclusive;

or a pharmaceutically acceptable salt thereof.

In a preferred embodiment the present invention is concerned with compounds according to formula (I) as defined in paragraphs [021]-[075], wherein:

$A^3$ is Acc or Aib, or a D- or L-amino acid selected from the list of amino acids consisting of Ile, Leu, Nle, Tle, hLeu, Cha, Val, Ala, Nva, and Abu, or is deleted;

$A^4$ is Acc, Aib, or Apc, or a D- or L-amino acid selected from the list of amino acids consisting of Lys, Arg, hArg, Orn, Dab, Dap, and HN—CH$((CH_2)_n$—N$(R^4R^5))$—C(O), or is deleted;

$A^5$ is Inc or a D- or L-amino acid selected from the list of amino acids consisting of Pro, Thz, Dmt, Dhp, Ktp, 4Hyp, 3Hyp, Pip, Tic, and Oic, or is deleted;

$A^6$ is Acc or a D- or L-amino acid selected from the list of amino acids consisting of Glu, Asp, Gln, Asn, Lys, Arg, Orn, Dab, Dap, and hArg, or is deleted;

$A^7$ is Acc, Act, Aib, Apc, or Gly, or a D- or L-amino acid selected from the list of amino acids consisting of Ala, Abu, Val, and Nva, or is deleted;

$A^8$ is Inc or a D- or L-amino acid selected from the list of amino acids consisting of Pro, Thz, Dmt, Dhp, Ktp, 4Hyp, 3Hyp, Pip, Tic, and Oic, or is deleted;

$A^9$ is Acc, Aib, or Gly or D- or L-Ala, or is deleted;

$A^{10}$ is Acc or a D- or L-amino acid selected from the list of amino acids consisting of Glu, Asp, Gln, and Asn, or is deleted;

$A^{11}$ is Acc or a D- or L-amino acid selected from the list of amino acids consisting of Asp, Glu, Gln, and Asn, or is deleted;

$A^{12}$ is Acc, Act, Aib, or Apc, or a D- or L-amino acid selected from the list of amino acids consisting of Ala, Gly, Abu, Val, and Nva, or is deleted;

$A^{13}$ is Acc, Act, or Aib, or a D- or L-amino acid selected from the list of amino acids consisting of Ser, Thr, Ala, Abu, and Val, or is deleted;

$A^{14}$ is Inc or a D- or L-amino acid selected from the list of amino acids consisting of Pro, Thz, Dmt, Dhp, Ktp, 4Hyp, 3Hyp, Pip, Tic, and Oic, or is deleted;

$A^{15}$ is Acc or a D- or L-amino acid selected from the list of amino acids consisting of Glu, Asp, Gln, and Asn, or is deleted;

$A^{16}$ is Acc or a D- or L-amino acid selected from the list of amino acids consisting of Glu, Asp, Gln, and Asn, or is deleted;

$A^{17}$ is Acc or Aib, or a D- or L-amino acid selected from the list of amino acids consisting of Leu, Ile, Nle, Tle, hLeu, Cha, Val, Ala, Nva, Abu, and Phe, or is deleted;

$A^{18}$ is Aib or Acc, or a D- or L-amino acid selected from the list of amino acids consisting of Asn, Gln, Glu, and Asp, or is deleted;

$A^{19}$ is Acc, Aib, or Apc, or a D- or L-amino acid selected from the list of amino acids consisting of Arg, hArg, Lys, Orn, Dab, Dap, and HN—CH$((CH_2)_n$—N$(R^4R^5))$—C(O), or is deleted;

$A^{20}$ is Acc or Aic, a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and ($X^1$, $X^2$,$X^3$,$X^4$,$X^5$)Phe, or is deleted;

$A^{21}$ is Acc or Aic, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and ($X^1$, $X^2$,$X^3$,$X^4$,$X^5$)Phe, or is deleted;

$A^{22}$ is Acc, Act, Aib, Apc, or Gly, or a D- or L-amino acid selected from the list of amino acids consisting of Ala, Abu, Val, and Nva, or is deleted;

$A^{23}$ is Acc, Act, or Aib, or a D- or L-amino acid selected from the list of amino acids consisting of Ser, Thr, Ala, Abu, and Val, or is deleted;

$A^{24}$ is Acc or Aib, or a D- or L-amino acid selected from the list of amino acids consisting of Leu, Ile, Nle, Tle, hLeu, Cha, Val, Ala, Nva, Abu, Trp, and Phe, or is deleted;

$A^{25}$ is Acc, Aib, or Apc, or a D- or L-amino acid selected from the list of amino acids consisting of Arg, hArg, Lys, Orn, Dab, Dap, and HN—CH(($CH_2$)$_n$—N($R^4R^5$))—C(O), or is deleted $A^{26}$ is Acc, Aib, or Apc, or a D- or L-amino acid selected from the list of amino acids consisting of His, 2Pal, 3Pal, 4Pal, Taz, 2Thi, 3Thi, 2Fua, HN—CH(($CH_2$)$_n$—N($R^4R^5$))-C(O), and ($X^1$,$X^2$,$X^3$,$X^4$,$X^5$-)Phe, or is deleted;

$A^{27}$ is Acc or Aic, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and ($X^1$, $X^2$,$X^3$,$X^4$,$X^5$)Phe;

$A^{28}$ is Acc or Aib, or a D- or L-amino acid selected from the list of amino acids consisting of Leu, Ile, Nle, Tle, hLeu, Trp, Cha, Val, Ala, Nva, Abu, and Phe;

$A^{29}$ is Acc or Aib, or a D- or L-amino acid selected from the list of amino acids consisting of Asn, Gln, Glu, Asp, and Trp;

$A^{30}$ is Acc or Aib, or a D- or L-amino acid selected from the list of amino acids consisting of Leu, Ile, Nle, Tle, hLeu, Trp, Cha, Val, Ala, Nva, Abu, and Phe;

$A^{31}$ is Acc or Aib, or a D- or L-amino acid selected from the list of amino acids consisting of Val, Leu, Ile, Nle, Tle, hLeu, Cha, Ala, Nva, Abu, Trp, and Phe;

$A^{32}$ is Acc, Act, or Aib, or a D- or L-amino acid selected from the list of amino acids consisting of Thr, Ser, Ala, Abu, Trp, and Val;

$A^{33}$ is Acc, Aib, or Apc, or a D- or L-amino acid selected from the list of amino acids consisting of Arg, hArg, Lys, Orn, Dab, Dap, and HN—CH(($CH_2$)$_n$—N($R^4R^5$))—C(O);

$A^{34}$ is Acc, Aib, Apc, or Glu, or a D- or L-amino acid selected from the list of amino acids consisting of Gln, Asn, and Asp;

$A^{35}$ is Acc, Aib, or Apc, or a D- or L-amino acid selected from the list of amino acids consisting of Arg, hArg, Lys, Orn, Dab, Dap, and HN—CH(($CH_2$)$_n$—N($R^4R^5$))—C(O); and $A^{36}$ is Acc, Aic, or Apc, or a D- or L-amino acid selected from the list of amino acids consisting of Tyr, Phe, hPhe, 2Thi, 3Thi, Taz, 2Fua, Trp, 2Nal, 1Nal, Cha, 2Pal, 3Pal, 4Pal, and ($X^1$,$X^2$,$X^3$,$X^4$,$X^5$)Phe;

or a pharmaceutically acceptable salt thereof.

In a more preferred embodiment the present invention is concerned with compounds according formula (I) as defined in paragraphs [021]-[075], wherein:

$A^3$ is Ile, Leu, Nle, Tle, hLeu, Cha, Val, Ala, Nva, Abu, Acc, or Aib, or is deleted;

$A^4$ is Lys, Arg, hArg, Orn, Dab, Dap, Apc, Aib, Acc, or HN—CH(($CH_2$)$_n$—N($R^4R^5$))—C(O), or is deleted;

$A^5$ is Pro, Thz, Dmt, Dhp, Ktp, 4Hyp, 3Hyp, Pip, Tic, Oic, or Inc, or is deleted;

$A^6$ is Glu, Asp, Gln, Asn, Lys, Arg, Orn, Dab, Dap, hArg, or Acc, or is deleted;

$A^7$ is Ala, Aib, Gly, Abu, Val, Nva, Apc, Act, or Acc, or is deleted;

$A^8$ is Pro, Thz, Dmt, Dhp, Ktp, 4Hyp, 3Hyp, Pip, Tic, Oic, or Inc, or is deleted;

$A^9$ is Gly, Ala, Aib, or Acc, or is deleted;

$A^{10}$ is Glu, Asp, Gln, Asn, or Acc, or is deleted;

$A^{11}$ is Asp, Glu, Gln, Asn, or Acc, or is deleted;

$A^{12}$ is Ala, Aib, Gly, Abu, Val, Nva, Apc, Act, or Acc, or is deleted;

$A^{13}$ is Ser, Thr, Aib, Act, Ala, Acc, Abu, or Val, or is deleted;

$A^{14}$ is Pro, Thz, Dmt, Dhp, Ktp, 4Hyp, 3Hyp, Pip, Tic, Oic, or Inc, or is deleted;

$A^{15}$ is Glu, Asp, Gln, Asn, or Acc, or is deleted;

$A^{16}$ is Glu, Asp, Gln, Asn, or Acc, or is deleted;

$A^{17}$ is Leu, Ile, Nle, Tle, hLeu, Cha, Val, Ala, Nva, Abu, Acc, Aib, or Phe, or is deleted;

$A^{18}$ is Asn, Gln, Glu, Asp, Aib, or Acc, or is deleted;

$A^{19}$ is Arg, hArg, Lys, Orn, Dab, Dap, Apc, Aib, Acc, or HN—CH(($CH_2$)$_n$—N($R^4R^5$))—C(O), or is deleted;

$A^{20}$ is Tyr, Phe, hPhe, 2Thi, 3Thi, Taz, 2Fua, Trp, 2Nal, 1Nal, Cha, 2Pal, 3Pal, 4Pal, ( )$X^1$,$X^2$,$X^3$,$X^4$,$X^5$)Phe, Acc, or Aic, or is deleted;

$A^{21}$ is Tyr, Phe, hPhe, 2Thi, 3Thi, Taz, 2Fua, Trp, 2Nal, 1Nal, Cha, 2Pal, 3Pal, 4Pal, ($X^1$,$X^2$,$X^3$,$X^4$,$X^5$)Phe, Acc, or Aic, or is deleted;

$A^{22}$ is Ala, Aib, Gly, Abu, Val, Nva, Apc, Act, Acc, or N-Me-Ala, or is deleted;

$A^{23}$ is Ser, Thr, Aib, Act, Ala, Acc, Abu, Val, or DTrp, or is deleted;

$A^{24}$ is Leu, Ile, Nle, Tle, hLeu, Cha, Val, Ala, Nva, Abu, Acc, Aib, Trp, or Phe, or is deleted;

$A^{25}$ is Arg, hArg, Lys, Orn, Dab, Dap, Apc, Aib, HN—CH(($CH_2$)$_n$—N($R^4R^5$))—C(O), or Acc, or is deleted;

$A^{26}$ is His, 2Pal, D2Pal, 3Pal, 4Pal, Taz, 2Thi, 3Thi, 2Fua, Apc, Aib, Acc, HN—CH(($CH_2$)$_n$—N($R^4R^5$))—C(O), or ($X^1$,$X^2$,$X^3$,$X^4$,$X^5$-)Phe, or is deleted;

$A^{27}$ is Tyr, Phe, hPhe, 2Thi, 3Thi, Taz, 2Fua, Trp, 2Nal, 1Nal, Cha, 2Pal, 3Pal, 4Pal, ($X^1$,$X^2$,$X^3$,$X^4$,$X^5$)Phe, Acc, or Aic;

$A^{28}$ is Leu, Ile, Nle, Tle, hLeu, Trp, Cha, Val, Ala, Nva, Abu, Acc, Aib, or Phe;

$A^{29}$ is Asn, Gln, Glu, Asp, Acc, Trp, or Aib;

$A^{30}$ is Leu, Ile, Nle, Tle, hLeu, Trp, Cha, Val, Ala, Nva, Abu, Acc, Aib, or Phe;

$A^{31}$ is Val, Leu, Ile, Nle, Tle, hLeu, Cha, Ala, Nva, Abu, Acc, Aib, Trp, or Phe;

$A^{32}$ is Thr, Ser, Aib, Act, Ala, Acc, Abu, Trp, DTrp, or Val;

$A^{33}$ is Arg, hArg, Lys, Orn, Dab, Dap, Apc, Aib, HN—CH(($CH_2$)$_n$—N($R^4R^5$))—C(O), or Acc;

$A^{34}$ is Gln, Asn, Glu, Asp, Acc, Aib, or Apc;

$A^{35}$ is Arg, hArg, Lys, Orn, Dab, Dap, Apc, Aib, HN—CH(($CH_2$)$_n$—N($R^4R^5$))—C(O), or Acc; and $A^{36}$ is, Tyr, Phe,. hPhe, 2Thi, 3Thi, Taz, 2Fua, Trp, 2Nal,: 1Nal, Cha, 2Pal, 3Pal, 4Pal, ($X^1$,$X^2$,$X^3$,$X^4$,$X^5$)Phe, Acc, Aic, or Apc;

or a pharmaceutically acceptable salt thereof.

In a still more preferred embodiment the present invention is concerned with compounds according formula (I) as defined in paragraphs [021]-[075], wherein:

$A^3$ is Ile, Leu, Nle, Val, Acc, or Aib, or is deleted;

$A^4$ is Lys, Arg, hArg, Orn, or Apc, or is deleted;

$A^5$ is Pro, Thz, Dmt, 4Hyp, or 3Hyp, or is deleted;

$A^6$ is Glu, Asp, Gln, or Acc, or is deleted;

$A^7$ is Ala, Aib, Abu, Act, or Acc, or is deleted;

$A^8$ is Pro, Thz, Dmt, 4Hyp, or 3Hyp, or is deleted;

A⁹ is Gly, Aib, or Acc, or is deleted;
A¹⁰ is Glu, Asp, Gln, or Acc or is deleted;
A¹¹ is Asp, Glu, Asn, or Acc or is deleted;
A¹² is Ala, Aib, Act, or Acc, or is deleted;
A¹³ is Ser, Thr, Aib, Act, or Acc, or is deleted;
A¹⁴ is Pro, Thz, Dmt, 4Hyp, or 3Hyp, or is deleted;
A¹⁵ is Glu, Asp, Gln, or Acc, or is deleted;
A¹⁶ is Glu, Asp, Gln, or Acc or is deleted;
A¹⁷ is Leu, Ile, Nle, Val, Acc, or Aib, or is deleted;
A¹⁸ is Asn, Gln, Asp, Aib, or Acc or is deleted;
A¹⁹ is Arg, hArg, Lys, or Apc, or is deleted;
A²⁰ is Tyr, Phe, 2Pal, 3Pal, 4Pal, (X¹,X²,X³,X⁴,X⁵)Phe, or Acc, or is deleted;
A²¹ is Tyr, Phe, 2Pal, 3Pal, 4Pal, (X¹,X²,X³,X⁴,X⁵)Phe, or Acc, or is deleted;
A²² is Ala, Aib, Abu, or Acc, or is deleted;
A²³ is Ser, Thr, Aib, Act, or Ala, or is deleted;
A²⁴ is Leu, Ile, Nle, Val, Acc, or Aib, or is deleted;
A²⁵ is Arg, hArg, Lys, or Apc, or is deleted;
A²⁶ is His, 2Pal, D2Pal, 3Pal, 4Pal, Taz, 2Thi, 3Thi, Apc, or (X¹,X²,X³,X⁴,X⁵-)Phe, or is deleted;
A²⁷ is Tyr, Phe, 2Pal, 3Pal, 4Pal, (X¹,X²,X³,X⁴,X⁵)Phe or Acc;
A²⁸ is Leu, Ile, Nle,-Val, Acc or Aib;
A²⁹ is Asn, Gln, Asp, Acc or Aib;
A³⁰ is Leu, Ile, Nle, Val, Acc or Aib;
A³¹ is Val, Leu, Ile, Ala, Acc or Aib;
A³² is Thr, Ser, Aib, Act or Acc;
A³³ is Arg, hArg, Lys or Apc;
A³⁴ is Gln, Asn, Glu, Aib or Apc;
A³⁵ is Arg, hArg, Lys or Apc; and
A³⁶ is Tyr, Phe, 2Pal, 3Pal, 4Pal, (X¹,X²,X³,X⁴,X⁵)Phe or Apc;
or a pharmaceutically acceptable salt thereof.

In yet a still more preferred embodiment the present invention is concerned with compounds according formula (I) as defined in paragraphs [021]-[075], wherein:
A³ is Ile or Acc, or is deleted;
A⁴ is Lys or Apc, or is deleted;
A⁵ is Pro or is deleted;
A⁶ is Glu or Acc, or is deleted;
A⁷ is Ala, Act, or Acc, or is deleted;
A⁸ is Pro or is deleted;
A⁹ is Gly or Acc, or is deleted;
A¹⁰ is Glu or Acc, or is deleted;
A¹¹ is Asp or Acc, or is deleted;
A¹² is Ala, Act, or Acc, or is deleted;
A¹³ is Ser, Act, or Acc, or is deleted;
A¹⁴ is Pro or is deleted;
A¹⁵ is Glu or Acc, or is deleted;
A¹⁶ is Glu or Acc, or is deleted;
A¹⁷ is Leu or Acc, or is deleted;
A¹⁸ is Asn or Acc, or is deleted;
A¹⁹ is Arg or Apc, or is deleted;
A²⁰ is Tyr, (X¹,X²,X³,X⁴,X⁵)Phe, or Acc, or is deleted;
A²¹ is Tyr, (X¹,X²,X³,X⁴ X⁵)Phe, or Acc, or is deleted;
A²² is Ala, Aib, or Acc, or is deleted;
A²³ is Ser or Act, or is deleted;
A²⁴ is Leu or Acc, or is deleted;
A²⁵ is Arg or Apc, or is deleted;
A²⁶ is His, 2Pal, D2Pal, 3Pal, 4Pal, Taz, Apc, or (X¹,X², X³,X⁴,X⁵-)Phe, or is deleted;
A²⁷ is Tyr, (X¹,X²,X³,X⁴,X⁵)Phe, or Acc;
A²⁸ is Leu, or Acc;
A²⁹ is Asn or Acc;
A³⁰ is Leu or Acc;
A³¹ is Val, Leu or Acc;
A³² is Thr, Act, or Acc;
A³³ is Arg or Apc;
A³⁴ is Gln or Apc;
A³⁵ is Arg or Apc; and
A³⁶ is Tyr, (X¹,X²,X³,X⁴,X⁵)Phe, or Apc;
or a pharmaceutically acceptable salt thereof.

In yet a still more preferred embodiment the present invention is concerned with compounds according formula (I) as defined in paragraphs [021]-[075], wherein:
Acc is, independently for each occurrence, A5c or A6c; and (X¹,X²,X³,X⁴,X⁵)Phe is, independently for each occurrence, (3,4,5-F)Phe or (2,3,4,5,6-F)Phe;
or a pharmaceutically acceptable salt thereof.

In yet a still more preferred embodiment the present invention is concerned withcompounds according formula (I) as defined in paragraphs [021]-[075], wherein:
A³ is Ile or is deleted;
A⁴ is Lys or is deleted;
A⁶ is Glu or is deleted;
A⁷ is Ala or is deleted;
A⁹ is Gly or is deleted;
A¹⁰ is Glu or is deleted;
A¹¹ is Asp or is deleted;
A¹² is Ala or is deleted;
A¹³ is Ser or is deleted;
A¹⁴ is Pro or is deleted;
A¹⁵ is Glu or is deleted;
A¹⁶ is Glu or is deleted;
A¹⁷ is Leu or is deleted;
A¹⁸ is Asn or is deleted;
A¹⁹ is Arg or is deleted;
A²⁰ is Tyr or is deleted;
A²¹ is Tyr or is deleted;
A²² is Ala, Aib, or A5c, or is deleted;
A²³ is Ser or is deleted;
A²⁴ is Leu or A6c;
A²⁵ is Arg;
A²⁶ is His, 2Pal, D2Pal, 3Pal, 4Pal, or Taz;
A²⁷ is Tyr or (3,4,5-F)Phe;
A²⁸ is Leu, or A6c;
A²⁹ is Asn;
A³⁰ is Leu or A6c;
A³¹ is Val, Leu, A5c or A6c;
A³² is Thr;
A³³ is Arg;
A³⁴ is Gln; and
A³⁶ is Tyr;
or a pharmaceutically acceptable salt thereof.

In yet a still more preferred embodiment the present invention is concerned with a compound according formula (I) as defined in paragraphs [021]-[075], wherein said compound is:
((2,3,4,5,6-F)Phe²⁰)hPYY(3-36)NH₂; (SEQ ID NO. 31)
((2,3,4,5,6-F)Phe²¹)hPYY(3-36)NH₂; (SEQ ID NO. 32)
Ac-((2,3,4,5,6-F)Phe²⁶)hPYY(22-36)NH₂; (SEQ ID NO. 33)
Ac-((2,3,4,5,6-F)Phe²⁶)hPYY(24-36)NH₂; (SEQ ID NO. 34)
((2,3,4,5,6-F)Phe²⁶)hPYY(3-36)NH₂; (SEQ ID NO. 35)
Ac-((2,3,4,5,6-F)Phe²⁷)hPYY(22-36)NH₂; (SEQ ID NO. 36)
Ac-((2,3,4,5,6-F)Phe²⁷)hPYY(24-36)NH₂; (SEQ ID NO. 37)
((2,3,4,5,6-F)Phe²⁷)hPYY(3-36)NH₂; (SEQ ID NO. 38)
Ac-((2,3,4,5,6-F)Phe³⁶)hPYY(22-36)NH₂; (SEQ ID NO. 39)

Ac-((2,3,4,5,6-F)Phe$^{36}$)hPYY(24-36)NH$_2$; (SEQ ID NO. 40)
((2,3,4,5,6-F)Phe$^{36}$)hPYY(3-36)NH$_2$; (SEQ ID NO. 41)
((3,4,5-F)Phe$^{20}$)hPYY(3-36)NH$_2$; (SEQ ID NO. 42)
((3,4,5-F)Phe$^{21}$)hPYY(3-36)NH$_2$; (SEQ ID NO. 43)
Ac-((3,4,5-F)Phe$^{26}$)hPYY(22-36)NH$_2$; (SEQ ID NO. 44)
Ac-((3,4,5-F)Phe$^{26}$)hPYY(24-36)NH$_2$; (SEQ ID NO. 45)
((3,4,5-F)Phe$^{26}$)hPYY(3-36)NH$_2$; (SEQ ID NO. 46)
Ac-((3,4,5-F)Phe$^{27}$)hPYY(22-36)NH$_2$; (SEQ ID NO. 15)
Ac-((3,4,5-F)Phe$^{27}$)hPYY(24-36)NH$_2$; (SEQ ID NO. 47)
((3,4,5-F)Phe$^{27}$)hPYY(3-36)NH$_2$; (SEQ ID NO. 12)
Ac-((3,4,5-F)Phe$^{36}$)hPYY(22-36)NH$_2$; (SEQ ID NO. 48)
Ac-((3,4,5-F)Phe36)hPYY(24-36)NH$_2$; (SEQ ID NO. 49)
((3,4,5-F)Phe36)hPYY(3-36)NH$_2$; (SEQ ID NO. 50)
Ac-(D2Pal$^{26}$)hPYY(22-36)NH$_2$; (SEQ ID NO. 26)
Ac-(2Pal$^{26}$)hPYY(22-36)NH$_2$; (SEQ ID NO. 27)
Ac-(2Pal$^{26}$, Leu$^{31}$)hPPY(24-36)NH$_2$; (SEQ ID NO. 18)
Ac-(3Pal$^{26}$)hPYY(22-36)NH$_2$; (SEQ ID NO. 14)
(3Pal$^{26}$)hPYY(3-36)NH$_2$; (SEQ ID NO. 5)
Ac-(3Pal$^{26}$, Leu$^{31}$)hPPY(24-36)NH$_2$; (SEQ ID NO. 16)
Ac-(4Pal$^{26}$)hPYY(22-36)NH$_2$; (SEQ ID NO. 13)
Ac-(4Pal$^{26}$, Leu$^{31}$)hPPY(24-36)NH$_2$; (SEQ ID NO. 17)
Ac-(A5c$^{22}$)hPYY(22-36)NH$_2$ (SEQ ID NO. 4)
Ac-(A5c$^{31}$)hPYY(22-36)NH$_2$; (SEQ ID NO. 24)
Ac-(A5c$^{31}$)hPYY(24-36)NH$_2$; (SEQ ID NO. 51)
(A5c$^{31}$)hPYY(3-36)NH$_2$ (SEQ ID NO. 3)
(A6c$^{10}$)hPYY(3-36)NH$_2$; (SEQ ID NO. 52)
(A6c$^{11}$)hPYY(3-36)NH$_2$; (SEQ ID NO. 53)
(A6c$^{12}$)hPYY(3-36)NH$_2$; (SEQ ID NO. 54)
(A6c$^{13}$)hPYY(3-36)NH$_2$; (SEQ ID NO. 55)
(A6c$^{15}$)hPYY(3-36)NH$_2$; (SEQ ID NO. 56)
(A6c$^{16}$)hPYY(3-36)NH$_2$; (SEQ ID NO. 57)
(A6c$^{17}$)hPYY(3-36)NH$_2$; (SEQ ID NO. 58)
(A6c$^{18}$)hPYY(3-36)NH$_2$; (SEQ ID NO. 59)
(A6c$^{20}$)hPYY(3-36)NH$_2$; (SEQ ID NO. 60)
(A6c$^{21}$)hPYY(3-36)NH$_2$; (SEQ ID NO. 61)
Ac-(A6c$^{22}$)hPYY(22-36)NH$_2$; (SEQ ID NO. 62)
(A6c$^{22}$)hPYY(3-36)NH$_2$; (SEQ ID NO. 63)
Ac-(A6c$^{24}$)hPYY(22-36)NH$_2$; (SEQ ID NO. 25)
Ac-(A6c$^{24}$)hPYY(24-36)NH$_2$; (SEQ ID NO. 64)
(A6C$^{24}$)hPYY(3-36)NH$_2$; (SEQ ID NO. 10)
Ac-(A6c$^{24}$, Leu$^{31}$)hPYY(24-36)NH$_2$; (SEQ ID NO. 28)
Ac-(A6c$^{27}$)hPYY(22-36)NH$_2$; (SEQ ID NO. 65)
Ac-(A6c$^{27}$)hPYY(24-36)NH$_2$; (SEQ ID NO. 66)
(A6c$^{27}$)hPYY(3-36)NH$_2$; (SEQ ID NO. 67)
Ac-(A6c$^{28}$)hPYY(22-36)NH$_2$; (SEQ ID NO. 23)
Ac-(A6c$^{28}$)hPYY(24-36)NH$_2$; (SEQ ID NO. 68)
(A6c$^{28}$)hPYY(3-36)NH$_2$; (SEQ ID NO. 8)
Ac-(A6c$^{28}$, Leu$^{31}$)hPYY(24-36)NH$_2$; (SEQ ID NO. 29)
Ac-(A6c$^{29}$)hPYY(22-36)NH$_2$; (SEQ ID NO. 69)
Ac-(A6c$^{29}$)hPYY(24-36)NH$_2$; (SEQ ID NO. 70)
(A6c$^{29}$)hPYY(3-36)NH$_2$; (SEQ ID NO. 71)
(A6c$^{3}$)hPYY(3-36)NH$_2$; (SEQ ID NO. 72)
Ac-(A6c$^{30}$)hPYY(22-36)NH$_2$; (SEQ ID NO. 22)
Ac-(A6c$^{30}$)hPYY(24-36)NH$_2$; (SEQ ID NO. 73)
(A6c$^{30}$)hPYY(3-36)NH$_2$; (SEQ ID NO. 9)
Ac-(A6c$^{31}$)hPYY(22-36)NH$_2$; .(SEQ ID NO. 21)
Ac-(A6c$^{31}$)hPYY(24-36)NH$_2$; (SEQ ID NO. 30)
(A6c$^{31}$)hPYY(3-36)NH$_2$; (SEQ ID NO. 74)
Ac-(A6c$^{32}$)hPYY(22-36)NH$_2$; (SEQ ID NO. 75)
Ac-(A6c$^{32}$)hPYY(24-36)NH$_2$; (SEQ ID NO. 76)
(A6c$^{32}$)hPYY(3-36)NH$_2$; (SEQ ID NO. 77)
(A6c$^{6}$)hPYY(3-36)NH$_2$; (SEQ ID NO. 78)
(A6c$^{7}$)hPYY(3-36)NH$_2$; (SEQ ID NO. 79)
(A6c$^{9}$)hPYY(3-36)NH$_2$; (SEQ ID NO. 80)
(Act$^{12}$)hPYY(3-36)NH$_2$; (SEQ ID NO. 81)
(Act$^{13}$)hPYY(3-36)NH$_2$; (SEQ ID NO. 82)
Ac-(Act$^{23}$)hPYY(22-36)NH$_2$; (SEQ ID NO. 83)
(Act$^{23}$)hPYY(3-36)NH$_2$; (SEQ ID NO. 84)
Ac-(Act$^{32}$)hPYY(22-36)NH$_2$; (SEQ ID NO. 85)
Ac-(Act$^{32}$)hPYY(24-36)NH$_2$; (SEQ ID NO. 86)
(Act$^{32}$)hPYY(3-36)NH$_2$; (SEQ ID NO. 87)
(Act$^{7}$)hPYY(3-36)NH$_2$; (SEQ ID NO. 88)
Ac-(Aib$^{22}$)hPYY(22-36)NH$_2$; (SEQ ID NO. 89)
(Aib$^{22}$)hPYY(3-36)NH$_2$; (SEQ ID NO. 11)
(Apc$^{19}$)hPYY(3-36)NH$_2$; (SEQ ID NO. 90)
Ac-(Apc$^{25}$)hPYY(22-36)NH$_2$; (SEQ ID NO. 91)
Ac-(Apc$^{25}$)hPYY(24-36)NH$_2$; (SEQ ID NO. 92)
(Apc$^{25}$)hPYY(3-36)NH$_2$; (SEQ ID NO. 93)
Ac-(Apc$^{26}$)hPYY(22-36)NH$_2$; (SEQ ID NO. 94)
Ac-(Apc$^{26}$)hPYY(24-36)NH$_2$; (SEQ ID NO. 95)
(Apc$^{26}$)hPYY(3-36)NH$_2$; (SEQ ID NO. 96)
Ac-(Apc$^{33}$)hPYY(22-36)NH$_2$; (SEQ ID NO. 97)
Ac-(Apc$^{33}$)hPYY(24-36)NH$_2$; (SEQ ID NO. 98)
(Apc$^{33}$)hPYY(3-36)NH$_2$; (SEQ ID NO. 99)
Ac-(Apc$^{34}$)hPYY(22-36)NH$_2$; (SEQ ID NO. 100)
Ac-(Apc$^{34}$)hPYY(24-36)NH$_2$; (SEQ ID NO. 101)
(Apc$^{34}$)hPYY(3-36)NH$_2$; (SEQ ID NO. 102)
Ac-(Apc$^{35}$)hPYY(22-36)NH$_2$; (SEQ ID NO. 103)
Ac-(Apc$^{35}$)hPYY(24-36)NH$_2$; (SEQ ID NO. 104)
(Apc$^{35}$)hPYY(3-36)NH$_2$; (SEQ ID NO. 7)
Ac-(Apc$^{36}$)hPYY(22-36)NH$_2$; (SEQ ID NO. 105)
Ac-(Apc$^{36}$)hPYY(24-36)NH$_2$; (SEQ ID NO. 106)
(Apc$^{36}$)hPYY(3-36)NH$_2$; (SEQ ID NO. 107)
(Apc$^{4}$)hPYY(3-36)NH$_2$; (SEQ ID NO. 108)
(Taz$^{26}$)hPYY(3-36)NH$_2$; (SEQ ID NO. 6)
Ac-(Taz$^{26}$)hPYY(22-36)NH$_2$; or (SEQ ID NO. 20)
Ac-(Taz$^{26}$, Leu$^{31}$)hPPY(24-36)NH$_2$; (SEQ ID NO. 19)
or a pharmaceutically acceptable salt thereof.

In yet a still more preferred embodiment the present invention is concerned with a compound according to the immediately foregoing list of compounds, wherein said compound is:

[A5C$^{31}$]hPYY(3-36)NH$_2$ (SEQ ID NO. 3)
Ac-[A5C$^{22}$]hPYY(22-36)NH$_2$ (SEQ ID NO. 4)
[3Pal$^{26}$]hPYY(3-36)NH$_2$; (SEQ ID NO. 5)
[Taz$^{26}$]hPYY(3-36)NH$_2$; (SEQ ID NO. 6)
[Apc$^{35}$]hPYY(3-36)NH$_2$; (SEQ ID NO. 7)
[A6C$^{28}$]hPYY(3-36)NH$_2$; (SEQ ID NO. 8)
[A6C$^{30}$]hPYY(3-36)NH$_2$; (SEQ ID NO. 9)
[A6C$^{24}$]hPYY(3-36)NH$_2$; (SEQ ID NO. 10)
[Aib$^{22}$]hPYY(3-36)NH$_2$; (SEQ ID NO. 11)
[((3,4,5-F)Phe)$^{27}$]hPYY(3-36)NH$_2$; (SEQ ID NO. 12)
Ac-[4Pal$^{26}$]hPYY(22-36)NH$_2$; (SEQ ID NO. 13)
Ac-[3Pal$^{26}$]hPYY(22-36)NH$_2$; (SEQ ID NO. 14)
Ac-[((3,4,5-F)Phe)$^{27}$]hPYY(22-36)NH$_2$; (SEQ ID NO. 15)
Ac-(3Pal$^{26}$, Leu$^{31}$)hPPY(24-36)NH$_2$; (SEQ ID NO. 16)
Ac-(4Pal$^{26}$, Leu$^{31}$)hPPY(24-36)NH$_2$; (SEQ ID NO. 17)
Ac-(2Pal$^{26}$, Leu$^{31}$)hPPY(24-36)NH$_2$; (SEQ ID NO. 18)
Ac-(Taz$^{26}$, Leu$^{31}$)hPPY(24-36)NH$_2$; (SEQ ID NO. 19)
Ac-[Taz26]hPYY(22-36)NH$_2$; (SEQ ID NO. 20)
Ac-[A6c$^{31}$]hPYY(22-36)NH$_2$; (SEQ ID NO. 21)
Ac-[A6c$^{30}$]hPYY(22-36)NH$_2$; (SEQ ID NO. 22)
Ac-[A6c$^{28}$]hPYY(22-36)NH$_2$; (SEQ ID NO. 23)
Ac-[A5c$^{31}$]hPYY(22-36)NH$_2$; (SEQ ID NO. 24)
Ac-[A6C$^{24}$]hPYY(22-36)NH$_2$; (SEQ ID NO. 25)
Ac-[D2Pal$^{26}$]hPYY(22-36)NH$_2$; (SEQ ID NO. 26)
Ac-[2Pal$^{26}$]hPYY(22-36)NH$_2$; (SEQ ID NO. 27)
Ac-[A6C$^{24}$, Leu$^{31}$]hPYY(24-36)NH$_2$; (SEQ ID NO. 28)
Ac-[A6C$^{28}$, Leu$^{31}$]hPYY(24-36)NH$_2$; or (SEQ ID NO. 29)
Ac-[A6C$^{31}$]hPYY(24-36)NH$_2$; (SEQ ID NO. 30)
Ac-(A6c$^{24}$)hPYY(24-36)NH$_2$; (SEQ ID NO. 64)
or a pharmaceutically acceptable salt thereof.

In yet a still more preferred embodiment the present invention is concerned with a compound according to the immediately foregoing list of compounds, wherein said compound is:
[A5C$^{31}$]hPYY(3-36)NH$_2$ (SEQ ID NO. 3)
[3Pal$^{26}$]hPYY(3-36)NH$_2$; (SEQ ID NO. 5)
[Taz$^{26}$]hPYY(3-36)NH$_2$; (SEQ ID NO. 6)
[A6C$^{28}$]hPYY(3-36)NH$_2$; (SEQ ID NO. 8)
[A6C$^{24}$]hPYY(3-36)NH$_2$; (SEQ ID NO. 10)
[Aib$^{22}$]hPYY(3-36)NH$_2$; (SEQ ID NO. 11)
[((3,4,5-F)Phe)$^{27}$]hPYY(3-36)NH$_2$; (SEQ ID NO. 12)
Ac-[4Pal$^{26}$]hPYY(22-36)NH$_2$; (SEQ ID NO. 13)
Ac-[3Pal$^{26}$]hPYY(22-36)NH$_2$; (SEQ ID NO. 14)
Ac-(3Pal$^{26}$, Leu$^{31}$)hPPY(24-36)NH$_2$; or (SEQ ID NO. 16)
Ac-(4Pal$^{26}$, Leu$^{31}$)hPPY(24-36)NH$_2$; (SEQ ID NO. 17)
or a pharmaceutically acceptable salt thereof.

In yet a still more preferred embodiment the present invention is concerned with a compound according to the immediately foregoing list of compounds, wherein saidcompound is:
[A5C$^{31}$]hPYY(3-36)NH$_2$ (SEQ ID NO. 3)
[3Pal$^{26}$]hPYY(3-36)NH$_2$; (SEQ ID NO. 5)
[Taz$^{26}$]hPYY(3-36)NH$_2$; (SEQ ID NO. 6)
[Apc$^{35}$]hPYY(3-36)NH$_2$; (SEQ ID NO. 7)
[A6C$^{28}$]hPYY(3-36)NH$_2$; (SEQ ID NO. 8)
[A6C$^{24}$]hPYY(3-36)NH$_2$; (SEQ ID NO. 10)
[Aib$^{22}$]hPYY(3-36)NH$_2$; (SEQ ID NO. 11)
Ac-[4Pal$^{26}$]hPYY(22-36)NH$_2$; (SEQ ID NO. 13)
Ac-[3Pal$^{26}$]hPYY(22-36)NH$_2$; (SEQ ID NO. 14)
Ac-(3Pal$^{26}$, Leu$^{31}$)hPPY(24-36)NH$_2$; (SEQ ID NO. 16)
Ac-(4Pal$^{26}$, Leu$^{31}$)hPPY(24-36)NH$_2$; or (SEQ ID NO. 17)
or a pharmaceutically acceptable salt thereof.

In yet a still more preferred embodiment the present invention is concerned with a compound according to the immediately foregoing list of compounds, wherein saidcompound is:
[A5C$^{31}$]hPYY(3-36)NH$_2$ (SEQ ID NO. 3)
[3Pal$^{26}$]hPYY(3-36)NH$_2$; (SEQ ID NO. 5)
[A6C$^{28}$]hPYY(3-36)NH$_2$; (SEQ ID NO. 8)
[A6C$^{24}$]hPYY(3-36)NH$_2$; or (SEQ ID NO. 10)
Ac-[4Pal$^{26}$]hPYY(22-36)NH$_2$; (SEQ ID NO. 13)
Ac-(A6c$^{24}$)hPYY(24-36)NH$_2$; (SEQ ID NO. 64)
or a pharmaceutically acceptable salt thereof.

In another aspect the present invention relates to a pharmaceutical composition comprising one or more compounds as defined in paragraphs [021] through [0428], or apharmaceutically acceptable salt thereof, and a pharmaceutically acceptable carrier.

In another aspect the present invention relates to a method of decreasing excess intestinal water and electrolyte secretion in a mammal in need thereof, said method comprising administering to said mammal an effective amount of one or more compounds as defined in paragraphs [021] through [0428], or a pharmaceutically acceptable salt thereof.

In another aspect the present invention relates to a method of regulating the proliferation of a cell type in a mammal in need thereof, said method comprising administering to said mammal an effective amount of one or more compounds as defined in paragraphs [021] through [0428], or a pharmaceutically acceptable salt thereof.

In preferred embodiments of the immediately preceding method said cell type is gastrointestinal cells and/or epithelial cells.

In another aspect the present invention relates to a method of augmenting nutrient transport in a mammal in need thereof, said method comprising administering to said mammal an effective amount of one or more compounds as defined in paragraphs [021] through [0428], or a pharmaceutically acceptable salt thereof.

In another aspect the present invention relates to a method of regulating lipolysis in a mammal in need thereof, said method comprising administering to said mammal an effective amount of one or more compounds as defined in paragraphs [021] through [0428], or a pharmaceutically acceptable salt thereof.

In another aspect the present invention relates to a method of regulating blood flow in a mammal in need thereof, said method comprising administering to said mammal an effective amount of one or more compounds as defined in paragraphs [021] through [0428], or a pharmaceutically acceptable salt thereof.

In another aspect the present invention relates to a method of facilitating weight loss, appetite decrease, weight maintenance, treating obesity, treating diabetes, treating complications of diabetes including retinopathy, or treating cardiovascular disorders in a mammal in need thereof, said method comprising administering to said mammal an effective amount of one or more compounds as defined in paragraphs [021] through [0428], or a pharmaceutically acceptable salt thereof.

In a preferred embodiment of the immediately preceding method said excessive weight is a contributing factor to a disease or condition including hypertension, diabetes, dyslipidemia, cardiovascular disease, gall stones, osteoarthritis and cancers.

In a more preferred embodiment of the immediately preceding method said facilitation of weight loss reduces the likelihood of such diseases or conditions or where said facilitation of weight loss comprises at least part of a treatment for such diseases or conditions.

In another aspect the present invention relates to a method of antagonizing the effects of PYY(3-36) in a mammal in need thereof, said method comprising administering to said mammal an effective amount of one or more compounds as defined in paragraphs [021] through [0428], or a pharmaceutically acceptable salt thereof, wherein said compound is a PYY antagonist.

In a preferred embodiment of the immediately preceding method said antagonist effects in said mammal comprise facilitating weight gain, facilitating maintenance in weight, and/or facilitating appetite increase.

In more a preferred embodiment of the immediately preceding method said facilitating weight gain, facilitating maintenance in weight, and/or facilitating appetite increase is indicated in a mammal having a disease or disorder, or under going a treatment, accompanied by weight loss.

In a still more preferred embodiment of the immediately preceding method said diseases or disorders accompanied by weight loss include anorexia, bulimia, cancer cachexia, AIDS, wasting, cachexia, and wasting in frail elderly, or said treatment accompanied by weight loss comprises chemotherapy, radiation therapy, temporary or permanent immobilization, or dialysis.

In another aspect, this invention is directed to radiolabeled analogs of formula (I). Preferably the analogs have a tyrosine residue iodinated on the phenyl ring, preferably at carbon position 3 or 5. The radioactive iodine is preferably I$^{125}$ or I$^{123}$. The chemistry associated with iodinated tyrosine residues within peptides is well known in the art of peptide chemistry. (See, e.g., European Patent Application 0389180, herein incorporated by reference.) Accordingly, radiolabeled PYY analogs can be used for assays in respect of PYY receptors, e.g., for competitive binding assays, for imaging cells containing PYY receptors, etc.

In another aspect, this invention is directed to a pharmaceutical composition comprising any one or more compounds

DETAILED DESCRIPTION

As set forth above and for convenience in describing this invention, the conventional and nonconventional abbreviations for the various amino acids are used. They are familiar to those skilled in the art, but for clarity are listed below. All peptide sequences mentioned herein are written according to the usual convention whereby the N-terminal amino acid is on the left and the C-terminal amino acid is on the right, unless noted otherwise.

Abbreviations (e.g. Ala) of amino acids in this disclosure stand for the structure —NH—C(R)(R')—CO—, wherein R and R' each is, independently, hydrogen or the side chain of an amino acid (e.g., R=CH$_3$ and R'=H for Ala), or R and R' may be joined to form a ring system. The term "N-methylated variant" refers to the same structure wherein the hydrogen atom attached to the nitrogen atom is replaced by methyl; i.e., —N(CH$_3$)—C(R)(R')—CO—. For the N-terminal amino acid, the abbreviation stands for the structure =N—C(R)(R')—CO—, wherein "=" represents the bonds to R$^2$ and R$^3$, defined herein.

A peptide of this invention is also denoted herein by another format, e.g., (A5C$^{31}$)hPYY(3-36)NH$_2$, with the substituted amino acid(s) from the natural sequence, (here, hPYY, i.e., human PYY) placed between the first set of parentheses (e.g., A5c$^{31}$ for Val$^{31}$ in hPYY(3-36)). The numbers between the second set of parentheses refer to the number of amino acids present in the peptide. For example, "hPYY(22-36)" refers to amino acids 22 through 36 of the peptide sequence for human PYY. The designation "NH$_2$" in, e.g., (A5C$^{31}$)hPYY(3-36)NH$_2$, indicates that the C-terminus of the peptide is amidated. (A5C$^{31}$)hPYY(3-36) or (A5C$^{31}$) hPYY(3-36)-OH, indicates that the C-terminus is the free acid.

| | |
|---|---|
| Abu | α-aminobutyric acid |
| Acc | 1-amino-1-cyclo(C$_3$-C$_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | 4-amino-4-carboxytetrahydropyran (i.e., the structure: 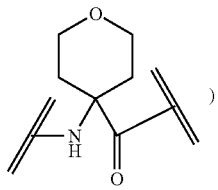 ) |
| Aib | α-aminoisobutyric acid |
| Aic | 2-aminoindan-2-carboxylic acid |
| Ala or A | alanine |
| β-Ala | beta-alanine |
| Apc | denotes the structure: |
| Arg or R | arginine |
| hArg | homoarginine |
| Asn or N | asparagine |
| Asp or D | aspartic acid |
| Cha | β-cyclohexylalanine |
| Cys or C | cysteine |
| Dab | 2,4-diaminobutyric acid |
| Dap | 2,3-diaminopropionic acid |
| Dhp | 3,4-dehydroproline |
| Dmt | 5,5-dimethylthiazolidine-4-carboxylic acid |
| 2Fua | β-(2-furyl)-alanine |
| Gln or Q | glutamine |
| Glu or E | glutamic acid |
| Gly or G | glycine |
| His or H | histidine |
| 3Hyp | trans-3-hydroxy-L-proline (i.e., (2S, 3S)-3-hydroxypyrrolidine-2-carboxylic acid) |
| 4Hyp | 4-hydroxyproline (i.e., (2S, 4R)-4-hydroxypyrrolidine-2-carboxylic acid) |
| Ile or I | isoleucine |
| Inc | indoline-2-carboxylic acid |
| Inp | isonipecotic acid |
| Ktp | 4-ketoproline |
| Leu or L | leucine |
| hLeu | homoleucine |
| Lys or K | lysine |
| Met or M | methionine |
| 1Nal | β-(1-naphthyl)alanine |
| 2Nal | β-(2-naphthyl)alanine |
| Nle | norleucine |
| Nva | norvaline |
| Oic | octahydroindole-2-carboxylic acid |
| Orn | ornithine |
| 2Pal | β-(2-pyridinyl)alanine |
| 3Pal | β-(3-pyridinyl)alanine |
| 4Pal | β-(4-pyridinyl)alanine |
| Phe or F | phenylalanine |
| hPhe | homophenylalanine |
| (3,4,5-F)Phe | 3,4,5-trifluorophenylalanine |
| (2,3,4,5,6-F)Phe | 2,3,4,5,6-pentafluorophenylalanine |
| Pip | pipecolic acid |
| Pro or P | proline |
| Ser or S | serine |
| Taz | β-(4-thiazolyl)alanine, i.e., |
| 2Thi | β-(2-thienyl)alanine |
| 3Thi | β-(3-thienyl)alanine |
| Thr or T | threonine |
| Thz | thiazolidine-4-carboxylic acid |
| Tic | 1,2,3,4-tetrahydroisoquinoline-3-carboxylic acid |
| Tle | tert-leucine |
| Trp or W | tryptophan |
| Tyr or Y | tyrosine |
| Val or V | valine |

Certain other abbreviations used herein are defined as follows:

| | |
|---|---|
| Ac: | acetyl |
| Boc: | tert-butyloxycarbonyl |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino}benzyl |
| DMAP: | 4-(dimethylamino)pyridine |
| DMF | N,N-dimethylformamide |
| DNP: | 2,4-dinitrophenyl |
| Fmoc: | Fluorenylmethyloxycarbonyl |
| HBTU: | 2-(1H-benzotriazole-1-yl)-1,1,3,3-tetramethyluronium hexafluorophosphate |
| cHex | cyclohexyl |
| HOAT: | O-(7-azabenzotriazol-1-yl)-1,1,3,3-tetramethyluronium hexafluorophosphate |
| HOBt: | 1-hydroxy-benzotriazole |
| Mmt: | 4-methoxytrityl |
| NMP: | N-methylpyrrolidone |
| Pbf: | 2,2,4,6,7-pentamethyldihydrobenzofuran-5-sulfonyl |
| tBu: | tert-butyl |
| TIS: | triisopropylsilane |
| TOS: | tosyl |
| trt | trityl |
| TFA: | trifluoro acetic acid |
| TFFH: | tetramethylfluoroforamidinium hexafluorophosphate |
| Z: | benzyloxycarbonyl |

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, (e.g., —CF$_3$, —C$_2$F$_4$, —C$_2$F$_5$, and the like), —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Non-limiting examples of alkyl acids containing, or consisting of, —(CH$_2$)$_{0-4}$—COOH, include 2-norbornane acetic acid, tert-butyric acid, 3-cyclopentyl propionic acid, and the like.

"Heteroalkyl" refers to an alkyl wherein one of more of the carbon atoms in the hydrocarbon group is/are replaced with one or more of the following groups: amino, amido, —O—, or carbonyl.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Alkynyl" refers to a hydrocarbon group made up of two or more carbons where one or more carbon-carbon triple bonds are present. The alkynyl hydrocarbon group may be straight-chain or contain one or more branches or cyclic groups.

"Substituted alkynyl" refers to an alkynyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Preferred examples of aryl include phenyl, 1-naphthyl, 2-naphthyl, indole, quinoline, 2-imidazole, and 9-anthracene. Aryl substituents are selected from the group consisting of —C$_{1-4}$ alkyl, —C$_{1-4}$ alkoxy, halogen (i.e., fluorine; chlorine, bromine, and iodine), —OH, —CN, —SH, —NH$_2$, —NO$_2$, —C$_{1-2}$ alkyl substituted with 1 to 5 halogens, —CF$_3$, —OCF$_3$, and —(CH$_2$)$_{0-4}$—COOH. In different embodiments the aryl contains 0, 1,2, 3, or 4 substituents.

"Arylalkyl" refers to an "alkyl" joined to an "aryl".

"Acyl" refers to R"—C(O)—, where R" is H, alkyl, substituted alkyl, heteroalkyl, substituted heteroalkyl, alkenyl, substituted alkenyl, alkynyl, substituted alkynyl, aryl, alkylaryl, substituted alklyaryl.

The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. An example of a procedure for obtaining a pharmaceutically acceptable salt of a compound of this invention, more particularly the HCl salt, is as follows. A purified peptide is dissolved in 0.1% HCl—H$_2$O, loaded onto a semi-preparative reverse phase column (250×10 mm, 10 μM particle size, 300A pore size), and eluted with a gradient of 0-100% 0.1% HCl—CH$_3$CN in 0.1% HCl—H$_2$O. The fractions containing the peptide peak are combined, concentrated and lyophilized to obtain the HCl salt of the peptide.

A compound of the present invention can be made into compositions in the form of a liquid, pill, tablet, or capsule for oral administration; a liquid capable of being administered nasally as drops or spray or a liquid for intravenous, subcutaneous, parenteral, intraperitoneal or rectal administration. The therapeutic composition can also be in the form of an oil emulsion or dispersion in conjunction with a lipophilic salt such as pamoic acid, or in the form of a biodegradable sustained-release composition for subcutaneous or intramuscular administration.

The compounds of the invention exhibit a broad range of biological activities related to their antisecretory and antimotility properties. While not wishing to be bound to any particular theory regarding the mechanism of action, it is believed that the compounds suppress gastrointestinal secretions by direct interaction with epithelial cells and/or by inhibiting secretion of hormones or neurotransmitters which stimulate intestinal secretion. The compounds of the invention may also control intestinal blood flow which in turn may modulate intestinal hydrostatic pressure in favor of net water absorption.

The compounds of the invention are especially useful in the treatment of any number of gastrointestinal disorders that are associated with excess intestinal electrlytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g. Harrison's principles of Internal Medicine, McGraw Hill Inc., New York, 12th ed.). Examples of infectious diarrhea include, without limitation, acute viral diarrhea, acute bacterial diarrhea (e.g., *salmonella, campylobacter*, and *clostridium*) or diarrhea due to protozoal infections, or travellers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera. Furthermore, the compounds of the invention can be used to treat intestinal dysfunction in patients with Acquired Immune Deficiency Syndrome (AIDS), especially during cachexia.

The compounds of the invention are also useful for inhibiting small intestinal fluid and electrolyte secretion, and augmenting nutrient transport, as well as increasing cell proliferation in the gastrointestinal tract, regulating lipolysis in, e.g., adipose tissue and regulating blood flow in a mammal.

The compounds of the invention are advantageous because they are truncated versions of the natural PYY peptide; thus, the shorter peptide not only facilitates easier synthesis and purification of the compounds, but also improves and reduces manufacturing procedures and expenses. Moreover, a shorter PYY compound is advantageous because such peptides will interact solely with PYY receptors and not with homologous receptors such as NPY Y1, Y3 and Y-5, thus minimizing unwanted agonist or antagonist side reactions.

The compounds of the invention can be and were produced using the techniques disclosed in the examples herein as well as techniques that are well known in the art. For example, a polypeptide region of a PYY analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989. Techniques for chemical synthesis of polypeptides are also well known in the art. (See e.g., Vincent in *Peptide and Protein Drug Delivery*, New York, N.Y., Dekker, 1990; For example, the peptides of this invention can be prepared by standard solid phase peptide synthesis. (See, e.g., Stewart, J. M., et al., *Solid Phase Synthesis*, 2$^{nd}$ Edition, Pierce Chemical Co., 1984.)

The substituents $R^2$ and $R^3$ of the above generic formula may be attached to thefree amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., R"—C(O)—, may be attached by coupling the free acid, e.g., R"COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

Peptides can be and were synthesized on an Applied Biosystems model 433A peptide synthesizer (Foster City, Calif.) using Fluorenylmethyloxycarbonyl (Fmoc) chemistry. Rink Amide 4-methylbenzylhydrylamine (MBHA) resin is used to obtain peptide amides (e.g. Example 1 below). Wang resin is used to obtain peptide acids. Rink Amide resin (substitution=0.72 mmol/g) or Wang resin (substitution=0.5 mmol/g) is placed in thereaction vessel of the synthesizer. The amino acids (4 equivalents) are sequentially coupledto the resin with the coupling reagents of 2-(1-H-benzotriazole-1-yl)-1,1,2,3-tetramethyluronium hexafluorophosphate (HBTU) (3.8 equivalents), 1-hydroxy-benzotriazole (HOBT) (3.8 equivalents), and diisopropylethylamine (DIEA) (1 mL) in NMP.

When $R^1$ is NH—$X^6$—$CH_2$—$CONH_2$, (i.e., $Z^0$=$CONH_2$), the synthesis of the peptide starts with Fmoc-HN—$X^6$—$CH_2$—COOH which is coupled to the Rink Amide MBHA resin. If $R^1$ is NH—$X^6$—$CH_2$—COOH, (i.e., $Z^0$=COOH) the synthesis of the peptide starts with Fmoc-HN—$X^6$—$CH_2$—COOH which is coupled to Wang resin. For this particular step, 4 molar equivalents of Fmoc-HN—$X^6$—COOH, HBTU and HOBt and 10 molar equivalents of DIEA are used. The coupling time is about 2 hours.

At the end of peptide synthesis, the Fmoc-group is removed. In some cases the free alpha amino group is then acylated with a suitable acylating agent. For example, the acylation may be carried out using about 2 equivalents of acetic anhydride until the ninhydrin test is negative. (See example 2.)

The peptide-resin is then treated with a mixture of TFA, $H_2O$ and triisopropylsilane (TIS) (VNN, 9.5/0.85/0.8) for about 4 h. The resin is filtered off and the filtrate is poured into ether. The precipitate is collected by filtration and washed thoroughly with ether. This crude product is dissolved in a mixed solvent system of acetonitrile and aqueous acetic acid and purified on a reverse-phase preparative HPLC system. The fractions are checked by analytical HPLC and those containing pure product are pooled and lyophilized to dryness.

EXAMPLES

Example 1

[A5C$^{31}$]hPYY(3-36)NH$_2$ (SEQ ID NO. 3)

The titled protected peptide was synthesized on an Applied Biosystems model 433A peptide synthesizer (Foster City, Calif.) using Fluorenylmethyloxycarbonyl (Fmoc) chemistry. A Rink Amide 4-methylbenzylhydrylamine (MBHA) resin (Novabiochem., San Diego, Calif.) with substitution of 0.72 mmol/g was used. The Fmoc amino acids (AnaSpec, San Jose, Calif.) used were Fmco-Tyr(tBu)-OH, Fmoc-Arg(Pbf)-OH, Fmoc-Gln(Trt)-OH, Fmoc-Thr(tBu)-OH, Fmoc-A5C—Fmoc-1-aminocyclopentanecarboxylic acid), Fmoc-Leu-OH, Fmoc-Asn(Trt)-OH, Fmoc-His(Trt)-OH, Fmoc-Ser(tBu)-OH, Fmoc-Ala-OH, Fmoc-Glu(tBu)-OH, Fmoc-Pro-OH, Fmoc-Asp(tBu)-OH, Fmoc-Gly-OH, Fmoc-Lys(Boc)-OH, and Fmoc-Ile-OH. The synthesis was carried out on a 0.25 mmol scale. The Fmoc groups were removed by treatment with 20% piperidine in N-methylpyrrolidone (NMP) for 30 min. In each coupling step, the Fmoc amino acid (4 eq, 1 mmol) was first pre-activated in 2 mL solution of 0.45M 2-(1-H-benzotriazole-1-yl)-1,1,2,3-tetramethyluronium hexafluorophosphate/1-hydroxy-benzotriazole (HBTU/HOBT) in NMP. This activated amino acid ester, 1 mL of diisopropylethylamine (DIEA) and 1 mL of NMP were added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h. The resin was coupled successively according to the sequence of the title peptide. After the peptide chain was assembled, the Fmoc group was removed and the resin was washed completely by using N,N-dimethylformamide (DMF) and dichloromethane (DCM).

At the end of the assembly of the peptide chain, the peptide-resin was transferred to a reaction vessel on a shaker and treated with a mixture of TFA, H$_2$O and triisopropylsilane (TIS) (9.5 mL/0.85 mL/0.8 mL) for 4 h. The resin was filtered off and the filtrate was poured into 200 mL of ether. The precipitate was collected by filtration and washed thoroughly with ether. This crude product was dissolved in a mixture of acetonitrile and aqueous acetic acid solution and purified on a reverse-phase preparative HPLC system with a column (4×43 cm) of C$_{18}$ DYNAMAX-100 A$^0$ (Varian, Walnut Creek, Calif.). The column was eluted over approximately 1 hour using a linear gradient of 95% A:5% B to 55% A:45% B, where A was 0.1% TFA in water and B was 0.1% TFA in acetonitrile. The fractions were checked by analytical HPLC and those containing pure product were pooled and lyophilized to dryness. Purity was assayed using HPLC and found to be approximately 97.6%. Electro-spray ionization mass spectrometry (ESI-MS) analysis gave the molecular weight at 4060.7 (in agreement with the calculated molecular weight of 4061.51).

Example 2

Ac-[A5C$^{22}$]hPYY(22-36)NH$_2$ (SEQ ID NO 4)

The titled peptide was synthesized and purified substantially according to the procedures described in Example 1. For the last coupling step, 2 mL of NMP solution containing 94 μL of Ac$_2$O, 44 μL of DIEA and 4 mg of HOBt was used to cap the N-terminal amino group with an acetyl functional group. The coupling time for this step was 30 min. Purity of the final acylated peptide was 99.9% based upon HPLC analysis. Electro-spray ionization mass spectrometry (ESI MS) analysis gave the molecular weight at 1970.9 (in agreement with the calculated molecular weight of 1971.29).

Examples 3-28

Examples 3 -28 can be and were prepared substantially according to the procedures disclosed in Examples 1 and 2, above.

| Ex. | Compound | SEQ ID NO. | Purity (HPLC) | Mol. Wt. (ESI-MS) | Mol. Wt. (Calculated) |
|---|---|---|---|---|---|
| 3. | [3Pal$^{26}$]hPYY(3-36)NH$_2$ | 5 | 99.9 | 4060.0 | 4060.5 |
| 4. | [Taz$^{26}$]hPYY(3-36)NH$_2$ | 6 | 95.6 | 4066.2 | 4066.6 |
| 5. | [Apc$^{35}$]hPYY(3-36)NH$_2$ | 7 | 94.1 | 4019.0 | 4019.5 |
| 6. | [A6C$^{28}$]hPYY(3-36)NH$_2$ | 8 | 96.8 | 4062.0 | 4061.5 |
| 7. | [A6C$^{30}$]hPYY(3-36)NH$_2$ | 9 | 99.9 | 4062.0 | 4061.5 |
| 8. | [A6C$^{24}$]hPYY(3-36)NH$_2$ | 10 | 96.5 | 4062.0 | 4061.5 |
| 9. | [Aib$^{22}$]hPYY(3-36)NH$_2$ | 11 | 97.7 | 4064.0 | 4063.5 |
| 10. | [(3,4,5-F)Phe$^{27}$]hPYY(3-36)NH$_2$ | 12 | 99.9 | 4087.2 | 4087.5 |
| 11. | Ac-[4Pal$^{26}$]hPYY(22-36)NH$_2$ | 13 | 99.9 | 1942.0 | 1942.3 |
| 12. | Ac-[3Pal$^{26}$]hPYY(22-36)NH$_2$ | 14 | 99.0 | 1941.7 | 1942.3 |
| 13. | Ac-[(3,4,5-F)Phe$^{27}$]hPYY(22-36)NH$_2$ | 15 | 100 | 1969.2 | 1969.2 |
| 14. | Ac-(3Pal$^{26}$, Leu$^{31}$)hPPY(24-36)NH$_2$ | 16 | 97.2 | 1797.7 | 1798.1 |
| 15. | Ac-(4Pal$^{26}$, Leu$^{31}$)hPPY(24-36)NH$_2$ | 17 | 97.0 | 1797.7 | 1798.1 |
| 16. | Ac-(2Pal$^{26}$, Leu$^{31}$)hPPY(24-36)NH$_2$ | 18 | 94.8 | 1797.9 | 1798.1 |
| 17. | Ac-(Taz$^{26}$, Leu$^{31}$)hPPY(24-36)NH$_2$ | 19 | 97.9 | 1803.4 | 1804.2 |
| 18. | Ac-[Taz$^{26}$]hPYY(22-36)NH$_2$ | 20 | 97.9 | 1948.3 | 1948.3 |
| 19. | Ac-[A6c$^{31}$]hPYY(22-36)NH$_2$ | 21 | 99.9 | 1957.2 | 1957.3 |
| 20. | Ac-[A6c$^{30}$]hPYY(22-36)NH$_2$ | 22 | 99.0 | 1942.9 | 1943.2 |
| 21. | Ac-[A6c$^{28}$]hPYY(22-36)NH$_2$ | 23 | 99.9 | 1942.8 | 1943.2 |
| 22. | Ac-[A5c$^{31}$]hPYY(22-36)NH$_2$ | 24 | 99.9 | 1942.6 | 1943.2 |
| 23. | Ac-[A6C$^{24}$]hPYY(22-36)NH$_2$ | 25 | 99.9 | 1943.2 | 1943.2 |
| 24. | Ac-[D2Pal$^{26}$]hPYY(22-36)NH$_2$ | 26 | 96.0 | 1941.9 | 1942.3 |
| 25. | Ac-[2Pal$^{26}$]hPYY(22-36)NH$_2$ | 27 | 99.6 | 1941.8 | 1942.3 |
| 26. | Ac-[A6C$^{24}$, Leu$^{31}$]hPYY(24-36)NH$_2$ | 28 | 98.8 | 1798.9 | 1799.1 |
| 27. | Ac-[A6C$^{28}$, Leu$^{31}$]hPYY(24-36)NH$_2$ | 29 | 97.5 | 1798.9 | 1799.1 |
| 28. | Ac-[A6C$^{31}$]hPYY(24-36)NH$_2$ | 30 | 96.3 | 1798.9 | 1799.1 |

Examples 29-56

Radioligand Binding Assay

Human neuroblastoma cell lines, SK-N-MC and SK-N-BE2 (American Type Culture Collection, Rockville, Md.) were cultured in EMEM media containing 10% fetal calf serum and 5% chicken embryo extract in a humidified atmosphere (37° C.) of 90% air and 10% CO$_2$.

For the in vitro Y1 and Y2 radioligand binding assays, the appropriate cells (SK-N-MC for Y1; SK-N-BE2 for Y2) were harvested, homogenized (Polytron, setting 6, 15 sec) in ice-cold 50 mM Tris-HCl (Buffer A), and centrifuged twice at 39,000×g (10 min), with an intermediate resuspension in fresh buffer. The final pellets were resuspended in approximately 20 ml of 50 mM Tris-HCl containing 5.0 mM $MgCl_2$, 0.1 mg/ml bacitracin, and 0.1% BSA (Buffer B), and held on ice for the receptor binding assay.

For assay, aliquots (0.4 ml) of the foregoing suspensions were incubated with 0.05 ml of 0.05 nM [$^{125}$I-Leu$^{31}$, Pro$^{34}$] PYY (Y1 receptor) or [$^{125}$I]PYY(3-36) (Y2 receptor), (each ~2200 Ci/mmol, New England Nuclear) in Buffer B, with or without 0.05 ml a solution (ranging from 0.01 nM -1000 nM) of an unlabeled competing peptide. After a 120 min incubation (25° C.), the bound radioligand was separated from the free by rapid filtration through GF/C filters, previously soaked in 0.3% polyethyleneimine. The filters were then washed three times with 5-ml aliquots of ice-cold Buffer A. Specific binding was defined as the total PYY radioligand bound minus that bound in the presence of 1 µM unlabeled PYY. Inhibition constants ($K_i$,) were calculated using the well-known Cheng-Prusoff equation.

Each of the compounds of Examples 1-28 was subjected to the immediately foregoing radioligand assay and was found to have, for the Y2 receptor, a $K_i$ of under 1000 nM, and for the Y1 receptor, a $K_i$ of under 2000 nM. Nearly all of the compounds of Examples 1-18 had $K_i$ values of under 30 nM for the Y2 receptor and under 300 nM for the Y1 receptor.

Antisecretory Effects; Intestinal Water and Sodium Absorption

The antisecretory effects and the effects on intestinal water and sodium absorption may be studied using techniques well known to one of skill in the art. For example, antisecretory effects may be investigated using the jejunal mucosa/short-circuit current (SCC) technique as described by Cox et al., J. Physiol. 398:65, 1988, ("Cox") and detailed in U.S. Pat. No. 6,046,167, ("U.S. '167") while intestinal water and sodium absorption may be investigated using the ileal Thiry-Vela fistulae technique, also detailed in U.S. '167. The contents of each of Cox and U.S. '167 are incorporated herein by reference in their entirety.

In the practice of the method of the present invention, an effective amount of any one of the peptides of this invention or a combination of any of the peptides of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or either solid, liquid or gaseous dosage, including tablets and suspensions. The administration can be conducted in a single unit dosage form with continuous therapy or in a single dose therapy ad libitum.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of the compound of the present invention for treating the above-mentioned disorders varies depending upon the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". Thus, a typical administration is oral administration or parenteral administration. The daily dose in the case of oral administration is typically in the range of 0.1 to 100 mg/kg body weight, and the daily dose in the case of parenteral administration is typically in the range of 0.001 to 50 mg/kg body weight.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims. Also, all documents referred to herein are incorporated by reference into the present application as though fully set forth herein.

What is claimed is:

1. A compound wherein said compound is:
((2,3,4,5,6-F)Phe$^{20}$)hPYY(3-36)NH$_2$; (SEQ ID NO. 31)
((2,3,4,5,6-F)Phe$^{21}$)hPYY(3-36)NH$_2$; (SEQ ID NO. 32)
Ac-((2,3,4,5,6-F)Phe$^{26}$)hPYY(22-36)NH$_2$; (SEQ ID NO. 33)
Ac-((2,3,4,5,6-F)Phe$^{26}$)hPYY(24-36)NH$_2$; (SEQ ID NO. 34)
((2,3,4,5,6-F)Phe$^{26}$)hPYY(3-36)NH$_2$; (SEQ ID NO. 35)
Ac-((2,3,4,5,6-F)Phe$^{27}$)hPYY(22-36)NH$_2$; (SEQ ID NO. 36)
Ac-((2,3,4,5,6-F)Phe$^{27}$)hPYY(24-36)NH$_2$; (SEQ ID NO. 37)
((2,3,4,5,6-F)Phe$^{27}$)hPYY(3-36)NH$_2$; (SEQ ID NO. 38)
Ac-((2,3,4,5,6-F)Phe$^{36}$)hPYY(22-36)NH$_2$; (SEQ ID NO. 39)
Ac-((2,3,4,5,6-F)Phe$^{36}$)hPYY(24-36)NH$_2$; (SEQ ID NO. 40)
((2,3,4,5,6-F)Phe$^{36}$)hPYY(3-36)NH$_2$; (SEQ ID NO. 41)
((3,4,5-F)Phe$^{20}$)hPYY(3-36)NH$_2$; (SEQ ID NO. 42)
((3,4,5-F)Phe$^{21}$)hPYY(3-36)NH$_2$; (SEQ ID NO. 43)
Ac-((3,4,5-F)Phe$^{26}$)hPYY(22-36)NH$_2$; (SEQ ID NO. 44)
Ac-((3,4,5-F)Phe$^{26}$)hPYY(24-36)NH$_2$; (SEQ ID NO. 45)
((3,4,5-F)Phe$^{26}$)hPYY(3-36)NH$_2$; (SEQ ID NO. 46)
Ac-((3,4,5-F)Phe$^{27}$)hPYY(22-36)NH$_2$; (SEQ ID NO. 15)
Ac-((3,4,5-F)Phe$^{27}$)hPYY(24-36)NH$_2$; (SEQ ID NO. 47)
((3,4,5-F)Phe$^{27}$)hPYY(3-36)NH$_2$; (SEQ ID NO. 12)
Ac-((3,4,5-F)Phe$^{36}$)hPYY(22-36)NH$_2$; (SEQ ID NO. 48)
Ac-((3,4,5-F)Phe$^{36}$)hPYY(24-36)NH$_2$; (SEQ ID NO. 49)
((3,4,5-F)Phe$^{36}$)hPYY(3-36)NH$_2$; (SEQ ID NO. 50)
Ac-(D2Pal$^{26}$)hPYY(22-36)NH$_2$; (SEQ ID NO. 26)
Ac-(2Pal$^{26}$)hPYY(22-36)NH$_2$; (SEQ ID NO. 27)
Ac-(2Pal$^{26}$, Leu$^{31}$)hPPY(24-36)NH$_2$; (SEQ ID NO. 18)
Ac-(3Pal$^{26}$)hPYY(22-36)NH$_2$; (SEQ ID NO. 14)
(3Pal$^{26}$)hPYY(3-36)NH$_2$; (SEQ ID NO. 5)
Ac-(3Pal$^{26}$, Leu$^{31}$)hPPY(24-36)NH$_2$; (SEQ ID NO. 16)
Ac-(4Pal$^{26}$)hPYY(22-36)NH$_2$; (SEQ ID NO. 13)
Ac-(4Pal$^{26}$, Leu$^{31}$)hPPY(24-36)NH$_2$; (SEQ ID NO. 17)
Ac-(A5c$^{22}$)hPYY(22-36)NH$_2$ (SEQ ID NO. 4)
Ac-(A5c$^{31}$)hPYY(22-36)NH$_2$; (SEQ ID NO. 24)
Ac-(A5c$^{31}$)hPYY(24-36)NH$_2$; (SEQ ID NO. 51)
(A5c$^{31}$)hPYY(3-36)NH$_2$ (SEQ ID NO. 3)
(A6c$^{10}$)hPYY(3-36)NH$_2$; (SEQ ID NO. 52)
(A6c$^{11}$)hPYY(3-36)NH$_2$; (SEQ ID NO. 53)
(A6c$^{12}$)hPYY(3-36)NH$_2$; (SEQ ID NO. 54)
(A6c$^{13}$)hPYY(3-36)NH$_2$; (SEQ ID NO. 55)
(A6c$^{15}$)hPYY(3-36)NH$_2$; (SEQ ID NO. 56)
(A6c$^{16}$)hPYY(3-36)NH$_2$; (SEQ ID NO. 57)

(A6c¹⁷)hPYY(3-36)NH₂; (SEQ ID NO. 58)
(A6c¹⁸)hPYY(3-36)NH₂; (SEQ ID NO. 59)
(A6c²⁰)hPYY(3-36)NH₂; (SEQ ID NO. 60)
(A6c²¹)hPYY(3-36)NH₂; (SEQ ID NO. 61)
Ac-(A6c²²)hPYY(22-36)NH₂; (SEQ ID NO. 62)
(A6c²²)hPYY(3-36)NH₂; (SEQ ID NO. 63)
Ac-(A6c²⁴)hPYY(22-36)NH₂; (SEQ ID NO. 25)
Ac-(A6c²⁴)hPYY(24-36)NH₂; (SEQ ID NO. 64)
(A6C²⁴)hPYY(3-36)NH₂; (SEQ ID NO. 10)
Ac-(A6c²⁴, Leu³¹)hPYY(24-36)NH₂; (SEQ ID NO. 28)
Ac-(A6c²⁷)hPYY(22-36)NH₂; (SEQ ID NO. 65)
Ac-(A6c²⁷)hPYY(24-36)NH₂; (SEQ ID NO. 66)
(A6c²⁷)hPYY(3-36)NH₂; (SEQ ID NO. 67)
Ac-(A6c²⁸)hPYY(22-36)NH₂; (SEQ ID NO. 23)
Ac-(A6c²⁸)hPYY(24-36)NH₂; (SEQ ID NO. 68)
(A6c²⁸)hPYY(3-36)NH₂; (SEQ ID NO. 8)
Ac-(A6c²⁸, Leu³¹)hPYY(24-36)NH₂; (SEQ ID NO. 29)
Ac-(A6c²⁹)hPYY(22-36)NH₂; (SEQ ID NO. 69)
Ac-(A6c²⁹)hpYY(24-36)NH₂; (SEQ ID NO. 70)
(A6c²⁹)hPYY(3-36)NH₂; (SEQ ID NO. 71)
(A6c³)hPYY(3-36)NH₂; (SEQ ID NO. 72)
Ac-(A6c³⁰)hPYY(22-36)NH₂; (SEQ ID NO. 22)
Ac-(A6c³⁰)hPYY(24-36)NH₂; (SEQ ID NO. 73)
(A6c³⁰)hPYY(3-36)NH₂; (SEQ ID NO. 9)
Ac-(A6c³¹)hPYY(22-36)NH₂; (SEQ ID NO. 21)
Ac-(A6c³¹)hPYY(24-36)NH₂; (SEQ ID NO. 30)
(A6c³¹)hPYY(3-36)NH₂; (SEQ ID NO. 74)
Ac-(A6c³²)hPYY(22-36)NH₂; (SEQ ID NO. 75)
Ac-(A6c³²)hPYY(24-36)NH₂; (SEQ ID NO. 76)
(A6c³²)hPYY(3-36)NH₂; (SEQ ID NO. 77)
(A6c⁶)hPYY(3-36)NH₂; (SEQ ID NO. 78)
(A6c⁷)hPYY(3-36)NH₂; (SEQ ID NO. 79)
(A6c⁹)hPYY(3-36)NH₂; (SEQ ID NO. 80)
(Act¹²)hPYY(3-36)NH₂; (SEQ ID NO. 81)
(Act¹³)hPYY(3-36)NH₂; (SEQ ID NO. 82)
Ac-(Act²³)hPYY(22-36)NH₂; (SEQ ID NO. 83)
(Act²³)hPYY(3-36)NH₂; (SEQ ID NO. 84)
Ac-(Act³²)hPYY(22-36)NH₂; (SEQ ID NO. 85)
Ac-(Act³²)hPYY(24-36)NH₂; (SEQ ID NO. 86)
(Act³²)hPYY(3-36)NH₂; (SEQ ID NO. 87)
(Act⁷)hPYY(3-36)NH₂; (SEQ ID NO. 88)
Ac-(Aib²²)hPYY(22-36)NH₂; (SEQ ID NO. 89)
(Aib²²)hPYY(3-36)NH₂; (SEQ ID NO. 11)
(Apc ¹⁹)hPYY(3-36)NH₂; (SEQ ID NO. 90)
Ac-(Apc²⁵)hPYY(22-36)NH₂; (SEQ ID NO. 91)
Ac-(Apc²⁵)hPYY(24-36)NH₂; (SEQ ID NO. 92)
(Apc²⁵)hPYY(3-36)NH₂; (SEQ ID NO. 93)
Ac-(Apc²⁶)hPYY(22-36)NH₂; (SEQ ID NO. 94)
Ac-(Apc²⁶)hPYY(24-36)NH₂; (SEQ ID NO. 95)
(Apc²⁶)hPYY(3-36)NH₂; (SEQ ID NO. 96)
Ac-(Apc³³)hPYY(22-36)NH₂; (SEQ ID NO. 97)
Ac-(Apc³³)hPYY(24-36)NH₂; (SEQ ID NO. 98)
(Apc³³)hPYY(3-36)NH₂; (SEQ ID NO. 99)
Ac-(Apc³⁴)hPYY(22-36)NH₂; (SEQ ID NO. 100)
Ac-(Apc³⁴)hPYY(24-36)NH₂; (SEQ ID NO. 101)
(Apc³⁴)hPYY(3-36)NH₂; (SEQ ID NO. 102)
Ac-(Apc³⁵)hPYY(22-36)NH₂; (SEQ ID NO. 103)
Ac-(Apc³⁵)hPYY(24-36)NH₂; (SEQ ID NO. 104)
(Apc³⁵)hPYY(3-36)NH₂; (SEQ ID NO. 7)
Ac-(Apc³⁶)hPYY(22-36)NH₂; (SEQ ID NO. 105)
Ac-(Apc³⁶)hPYY(24-36)NH₂; (SEQ ID NO. 106)
(Apc³⁶)hPYY(3-36)NH₂; (SEQ ID NO. 107)
(Apc⁴)hPYY(3-36)NH₂; (SEQ ID NO. 108)
(Taz²⁶)hPYY(3-36)NH₂; (SEQ ID NO. 6)
Ac-(Taz²⁶)hPYY(22-36)NH₂; or (SEQ ID NO. 20)
Ac-(Taz²⁶, Leu³¹)hPPY(24-36)NH₂; (SEQ ID NO. 19) or
a pharmaceutically acceptable salt thereof.

2. A compound according to claim 1, wherein said compound is:
[A5C³¹]hPYY(3-36)NH₂ (SEQ ID NO. 3)
Ac-[A5C²²]hPYY(22-36)NH₂ (SEQ ID NO. 4)
[3Pal²⁶]hPYY(3-36)NH₂; (SEQ ID NO. 5)
[Taz²⁶]hPYY(3-36)NH₂; (SEQ ID NO. 6)
[Apc³⁵]hPYY(3-36)NH₂; (SEQ ID NO. 7)
[A6C²⁸]hPYY(3-36)NH₂; (SEQ ID NO. 8)
[A6C³⁰]hPYY(3-36)NH₂; (SEQ ID NO. 9)
[A6C²⁴]hPYY(3-36)NH₂; (SEQ ID NO. 10)
[Aib²²]hPYY(3-36)NH₂; (SEQ ID NO. 11)
[((3,4,5-F)Phe)²⁷]hPYY(3-36)NH₂; (SEQ ID NO. 12)
Ac-[4Pal²⁶]hPYY(22-36)NH₂; (SEQ ID NO. 13)
Ac-[3Pal²⁶]hPYY(22-36)NH₂; (SEQ ID NO. 14)
Ac-[((3,4,5-F)Phe)²⁷]hPYY(22-36)NH₂; (SEQ ID NO. 15)
Ac-(3Pal²⁶, Leu³¹)hPPY(24-36)NH₂; (SEQ ID NO. 16)
Ac-(4Pal²⁶, Leu³¹)hPPY(24-36)NH₂; (SEQ ID NO. 17)
Ac-(2Pal²⁶, Leu³¹)hPPY(24-36)NH₂; (SEQ ID NO. 18)
Ac-(Taz²⁶, Leu³¹)hPPY(24-36)NH₂; (SEQ ID NO. 19)
Ac-[Taz²⁶]hPYY(22-36)NH₂; (SEQ ID NO. 20)
Ac-[A6c³¹]hPYY(22-36)NH₂; (SEQ ID NO. 21)
Ac-[A6c³⁰]hPYY(22-36)NH₂; (SEQ ID NO. 22)
Ac-[A6c²⁸]hPYY(22-36)NH₂; (SEQ ID NO. 23)
Ac-[A5c³¹]hPYY(22-36)NH₂; (SEQ ID NO. 24)
Ac-[A6C²⁴]hPYY(22-36)NH₂; (SEQ ID NO. 25)
Ac-[D2Pal²⁶]hPYY(22-36)NH₂; (SEQ ID NO. 26)
Ac-[2Pal²⁶]hPYY(22-36)NH₂; (SEQ ID NO. 27)
Ac-[A6C²⁴, Leu³¹]hPYY(24-36)NH₂; (SEQ ID NO. 28)
Ac-[A6C²⁸, Leu³¹]hPYY(24-36)NH₂; (SEQ ID NO. 29)
Ac-[A6C³¹]hPYY(24-36)NH₂; or (SEQ ID NO. 30)
Ac-(A6c²⁴)hPYY(24-36)NH₂; (SEQ ID NO. 64) or a pharmaceutically acceptable salt thereof.

3. A compound according to claim 2, wherein said compound is:
[A5C³¹]hPYY(3-36)NH₂ (SEQ ID NO. 3)
[3Pal²⁶]hPYY(3-36)NH₂; (SEQ ID NO. 5)
[Taz²⁶]hPYY(3-36)NH₂; (SEQ ID NO. 6)
[A6C²⁸]hPYY(3-36)NH₂; (SEQ ID NO. 8)
[A6C²⁴]hPYY(3-36)NH₂; (SEQ ID NO. 10)
[Aib²²]hPYY(3-36)NH₂; (SEQ ID NO. 11)
[((3,4,5-F)Phe)²⁷]hPYY(3-36)NH₂; (SEQ ID NO. 12)
Ac-[4Pal²⁶]hPYY(22-36)NH₂; (SEQ ID NO. 13)
Ac-[3Pal²⁶]hPYY(22-36)NH₂; (SEQ ID NO. 14)
Ac-(3Pal²⁶, Leu³¹)hPPY(24-36)NH₂; or (SEQ ID NO. 16)
Ac-(4Pal²⁶, Leu³¹)hPPY(24-36)NH₂; (SEQ ID NO. 17) or
a pharmaceutically acceptable salt thereof.

4. A compound according to claim 2, wherein said compound is:
[A5C³¹]hPYY(3-36)NH₂ (SEQ ID NO. 3)
[3Pal²⁶]hPYY(3-36)NH₂; (SEQ ID NO. 5)
[Taz²⁶]hPYY(3-36)NH₂; (SEQ ID NO. 6)
[Apc³⁵]hPYY(3-36)NH₂; (SEQ ID NO. 7)
[A6C²⁸]hPYY(3-36)NH₂; (SEQ ID NO. 8)
[A6C²⁴]hPYY(3-36)NH₂; (SEQ ID NO. 10)
[Aib²²]hPYY(3-36)NH₂; (SEQ ID NO. 11)
Ac-[4Pal²⁶]hPYY(22-36)NH₂; (SEQ ID NO. 13)
Ac-[3Pal²⁶]hPYY(22-36)NH₂; (SEQ ID NO. 14)
Ac-(3Pal²⁶, Leu³¹)hPPY(24-36)NH₂; or (SEQ ID NO. 16)
Ac-(4Pal²⁶, Leu³¹)hPPY(24-36)NH₂; (SEQ ID NO. 17) or
a pharmaceutically acceptable salt thereof.

5. A compound according to claim 2, wherein said compound is:
[A5C³¹]hPYY(3-36)NH₂ (SEQ ID NO. 3)
[3Pal²⁶]hPYY(3-36)NH₂; (SEQ ID NO. 5)
[A6C²⁸]hPYY(3-36)NH₂; (SEQ ID NO. 8)
[A6C²⁴]hPYY(3-36)NH₂; (SEQ ID NO. 10)

Ac-[4Pal$^{26}$]hPYY(22-36)NH$_2$; or (SEQ ID NO. 13)
Ac-(A6c$^{24}$)hPYY(24-36)NH$_2$; (SEQ ID NO. 64) or a pharmaceutically acceptable salt thereof.

6. A pharmaceutical composition comprising a compound according to any one of claims 1-5, or a pharmaceutically acceptable salt thereof, and a pharmaceutically acceptable carrier.

7. A method of decreasing excess intestinal water and electrolyte secretion in a mammal in need thereof, said method comprising administering to said mammal an effective amount of a compound according to any one of claims 1-5, or a pharmaceutically acceptable salt thereof.

* * * * *